United States Patent
Akintelure et al.

(10) Patent No.: US 12,318,465 B2
(45) Date of Patent: *Jun. 3, 2025

(54) PERSONAL CARE COMPOSITIONS FOR CLEANSING THE SKIN

(71) Applicant: The Procter & Gamble Company, Cincinnati, OH (US)

(72) Inventors: Olubolaji Akintelure, Mason, OH (US); Karl Shiqing Wei, Mason, OH (US); Wei Ji, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,608

(22) Filed: Dec. 5, 2022

(65) Prior Publication Data

US 2023/0172827 A1 Jun. 8, 2023

Related U.S. Application Data

(60) Provisional application No. 63/286,318, filed on Dec. 6, 2021.

(51) Int. Cl.
*A61K 8/46* (2006.01)
*A61K 8/20* (2006.01)
(Continued)

(52) U.S. Cl.
CPC ............... *A61K 8/463* (2013.01); *A61K 8/20* (2013.01); *A61K 8/44* (2013.01); *A61Q 19/10* (2013.01);
(Continued)

(58) Field of Classification Search
CPC .......... A61Q 19/10; A61K 8/463; A61K 8/20; A61K 8/44; A61K 2800/30;
(Continued)

(56) References Cited

U.S. PATENT DOCUMENTS 7,666,825 B2 * 2/2010 Wagner .................... A61Q 5/02
510/156
8,084,407 B2 * 12/2011 Soffin ....................... A61Q 5/02
510/156

(Continued)

FOREIGN PATENT DOCUMENTS

| CA | 2643784 A1 | 2/2009 |
| EP | 2011545 A2 | 1/2009 |
| WO | 2022266175 A2 | 12/2022 |

OTHER PUBLICATIONS

PCT Search Report and Written Opinion for PCT/US2022/080718 dated Jun. 1, 2023, 15 pages.
(Continued)

*Primary Examiner* — Walter E Webb
*Assistant Examiner* — Amanda Michelle Petritsch
(74) *Attorney, Agent, or Firm* — Alexandra S. Anoff

(57) ABSTRACT

Described herein, personal care compositions, methods and uses. Personal care compositions include at least a cleansing phase and a benefit phase, wherein the cleansing phase comprises an aqueous structured surfactant phase. The cleansing phase comprises: a C13 alkyl sulfate anionic surfactant; a zwitterionic surfactant, wherein the zwitterionic surfactant comprises a betaine; a structuring system comprising: optionally, a non-ionic emulsifier; optionally, a rheology modifier; an electrolyte. The benefit phase comprises a benefit agent.

17 Claims, 3 Drawing Sheets

(51) Int. Cl.
*A61K 8/44* (2006.01)
*A61Q 19/10* (2006.01)

(52) U.S. Cl.
CPC ...... *A61K 2800/30* (2013.01); *A61K 2800/48* (2013.01); *A61K 2800/596* (2013.01)

(58) Field of Classification Search
CPC .......... A61K 2800/48; A61K 2800/596; A61K 8/062; A61K 8/49
See application file for complete search history.

(56) References Cited

U.S. PATENT DOCUMENTS

| | | | |
|---|---|---|---|
| 8,105,996 | B2 | 1/2012 | Wei |
| 8,158,566 | B2 | 4/2012 | Wei |
| 9,750,674 | B2 | 9/2017 | Wei et al. |
| 10,588,838 | B2 | 3/2020 | Wei |
| 11,807,829 | B2 | 11/2023 | Vinson |
| 11,932,827 | B2 | 3/2024 | Biiliauw |
| 12,029,803 | B2 * | 7/2024 | Akintelure ............ A61K 8/042 |
| 2006/0079417 | A1 | 4/2006 | Wagner |
| 2006/0079418 | A1 | 4/2006 | Wagner et al. |
| 2006/0210505 | A1 | 9/2006 | Clapp et al. |
| 2012/0316095 | A1 | 12/2012 | Wei |
| 2013/0029895 | A1 | 1/2013 | Bettiol et al. |
| 2013/0149273 | A1 | 6/2013 | Wei |
| 2016/0022565 | A1 | 1/2016 | Krause et al. |
| 2017/0333315 | A1 | 11/2017 | Wei |
| 2018/0110704 | A1 | 4/2018 | Zhao |
| 2018/0185255 | A1 | 7/2018 | Wei |
| 2019/0178774 | A1 | 6/2019 | Wei et al. |
| 2022/0081648 | A1 | 3/2022 | Billiauw et al. |
| 2024/0207154 | A1 | 6/2024 | Akintelure |

OTHER PUBLICATIONS

All Office Actions; U.S. Appl. No. 18/598,213, filed Mar. 7, 2024.
All Office Actions; U.S. Appl. No. 18/676,576, filed May 29, 2024.
Unpublished U.S. Appl. No. 18/598,213, filed Mar. 7, 2024, to Olubolaji Akintelure et. al.
Unpublished U.S. Appl. No. 18/676,576, filed May 29, 2024, to Olubolaji Akintelure et. al.
Anonymous; Database GNPD Mintel, "Hand Soap", XP055953965, Database accession No. 5833719, dated Jul. 18, 2018, 03 Pages.

* cited by examiner

PERSONAL CARE COMPOSITIONS FOR CLEANSING THE SKIN

FIELD OF THE INVENTION

The present application generally relates to personal care compositions for cleansing the skin, its methods and its uses. The personal care composition includes at least a cleansing phase and a benefit phase, wherein the cleansing phase comprises an aqueous structured surfactant phase. The cleansing phase comprises a C13 alkyl sulfate anionic surfactant, a zwitterionic surfactant that includes a betaine, and a structuring system. The benefit phase comprises a benefit agent.

BACKGROUND OF THE INVENTION

Cleansing is an activity that has been done for hundreds of years. Early cleansers were based on either soap chemistry or simple mechanical action in order to remove dirt from the skin, as well as endogenous soils such as sweat, sebum, and body odors. Skin cleansing and methods therefore have involved the utilization of soaps, body washes, and other personal care compositions. Personal care compositions can be structured to suspend and stabilize dispersions of benefit agents while maintaining physical integrity of the personal care compositions, and there are many ways to provide such structure. The ability to provide structure can be an important property for such personal care compositions, but it is also important for personal care compositions to have the ability to rapidly become micellar upon dilution for cleansing the skin and depositing benefit agents. Having too much structure in a personal care composition can result in poor performance while not having enough structure in a personal care composition can cause instability. Further, achieving a balance between these two properties can be a difficult task. Personal care compositions comprising sodium trideceth-2 sulfate and a structuring system based on specific associative polymers were explored.

Ethoxylated surfactants such as Sodium Laureth Sulfate (SLES or SLE3S) or Sodium Trideceth-n Sulfate (STnS) are used widely across the cosmetic industry in personal care products. These surfactants traditionally have been used to achieve a consumer desirable product profile which includes dispensed viscosity/product texture, lather, cleaning, and deposition of hair/scalp actives. Ethoxylation provides enhanced solubility, reduced crystallization in liquids, enhanced polymer interaction for coacervate formation and subsequent benefit delivery to the skin and scalp, increased mildness to the skin, and improved quality of lather.

Alkoxylated fatty alcohols are used are in many industries. For example, they can be used as non-ionic surfactants in detergents and cleansers. They can also be an intermediate in the production of other surfactants through processes like sulfation. Current sulfation processes of alkoxylated fatty alcohols can result in the formation of unwanted contaminants such as dioxane components which can remain as part of the alkoxylated fatty alcohol sulfate as it is sold or used. Such unwanted contaminants can be removed by additional treatment processes, e.g. a relatively and costly vacuum stripping process.

As such, there is a desire to make personal care compositions that contain relatively very low amount or no ethoxylated surfactants, to mitigate any undesired contaminant profile and any need of any additional treatment processes.

There is a need to develop a formulation approach for personal care compositions that utilize relatively very low or non-ethoxylated surfactants, without having negative consumer noticeable trade-offs, especially in terms of providing the desired balance between structure in the personal care compositions and performance.

There is a need to provide a personal care composition for cleansing the skin with an improved structure, an improved stability, with an optimum rheology profile, any attributes sought by the consumer such as lather performance, mildness, combatting any drying effects of the surfactants, deposition of benefit agents, enhanced fragrance experience and/or any improved skin-feel attributes such as skin feeling less oily and/or sticky.

SUMMARY OF THE INVENTION

A personal care composition is provided and comprises: at least a cleansing phase and a benefit phase, wherein the cleansing phase comprises an aqueous structured surfactant phase. The cleansing phase comprises: i) from about 1% to about 20%, preferably from about 2% to about 18%, more preferably from about 3% to about 15%, most preferably from about 4% to about 13% by weight of the personal care composition, of a C13 alkyl sulfate anionic surfactant, wherein the C13 alkyl sulfate anionic surfactant consists of: a) less than about 40% by weight of the C13 alkyl sulfate anionic surfactant of a linear C13 alkyl sulfate, and b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and c) less than about 5% by weight of the C13 alkyl sulfate anionic surfactant of other branched C13 alkyl sulfate anionic surfactant, wherein a, b and c add up to about 100% by weight of the C13 alkyl sulfate anionic surfactant; ii) from about 0.1% to about 20%, preferably from about 2% to about 10%, more preferably from about 3% to about 8%, most preferably from about 4% to about 7% by weight of the personal care composition, of a zwitterionic surfactant, wherein the zwitterionic surfactant comprises a betaine; iii a structuring system comprising: iiia) optionally, a non-ionic emulsifier; iiib) optionally, from about 0.01% to about 5%, preferably from about 0.1% to about 2%, more preferably from about 0.2% to about 1%, most preferably from about 0.5% to about 1% by weight of the personal care composition, of a rheology modifier; iiic) an electrolyte. The benefit phase comprises: from about 0.1% to about 50%, by weight of said personal care composition, of a benefit agent.

A method of increasing stability of a personal care composition is provided and comprises the step of forming a personal care composition as set out herein with a C13 alkyl sulfate anionic surfactant, wherein the C13 alkyl sulfate anionic surfactant consists of:

(a) less than about 40% by weight of the C13 alkyl sulfate anionic surfactant of a linear C13 alkyl sulfate, and
(b) more than about 60% by weight of the C13 alkyl sulfate anionic surfactant of a 2-branched C13 alkyl sulfate anionic surfactant, wherein the 2-branched C13 alkyl sulfate anionic surfactant comprises:
    about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and (c) less than about 5% by weight of the C13 alkyl sulfate anionic surfactant of other branched C13 alkyl sulfate anionic surfactant, wherein a, b and c add up to about 100% by weight of the C13 alkyl sulfate anionic surfactant.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definitions of Terms

Figure 1:
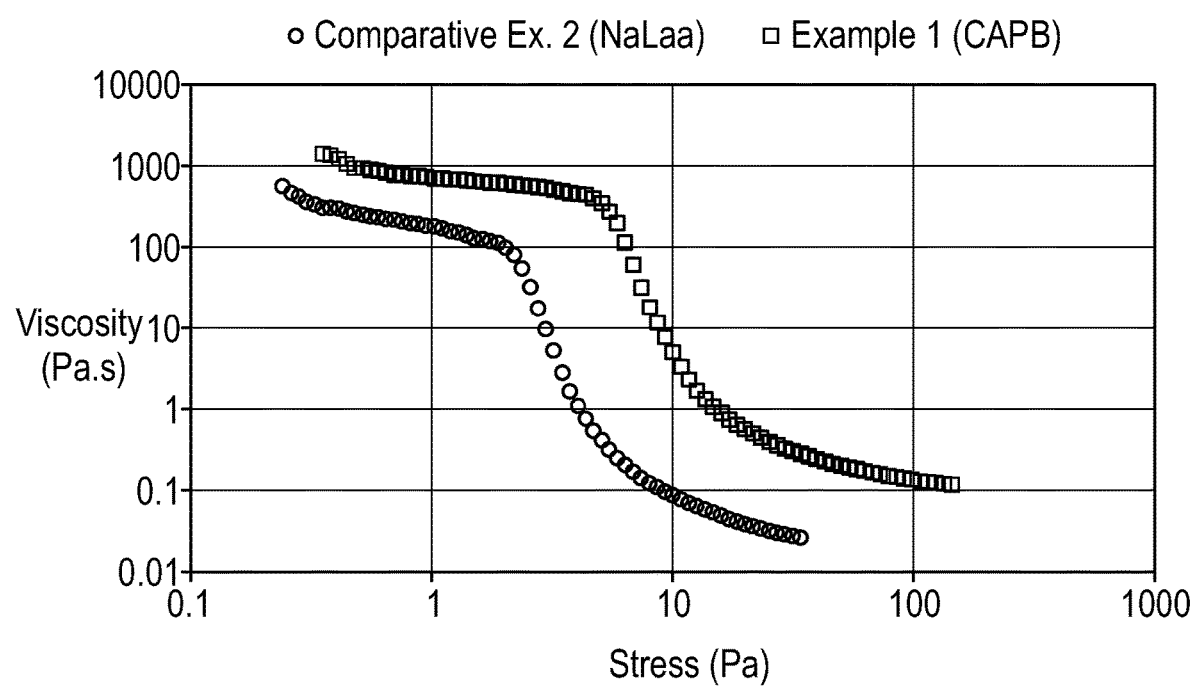
FIG. 1 is a graph of the rheology profile of the C13 alkyl sulfate anionic surfactant compositions with different co-surfactants (zwitterionic or amphoteric surfactants)

In this document, including in all embodiments of all aspects of the present invention, the following definitions apply unless specifically stated otherwise.

All percentages are by weight (w/w) of the composition, unless otherwise specified. "% wt." means percentage by weight. References to 'parts' e.g. a mixture of 1 part X and 3 parts Y, is a ratio by weight. All ratios or percentages are weight ratios or weight percentages unless specifically stated otherwise.

An "active composition" is the composition absent water, and an "active ingredient" is the ingredient absent its water "QS" or "QSP" means sufficient quantity for 100% or for 100 g.+/− indicates the standard deviation. All ranges are inclusive and combinable. The number of significant digits conveys neither a limitation on the indicated amounts nor on the accuracy of the measurements. All numerical amounts are understood to be modified by the word "about".

All measurements are understood to be made at 25° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level and do not include carriers or by-products that may be included in commercially available materials.

Herein, "comprising" means that other steps and other ingredients can be in addition. "Comprising" encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean "one or more" of what is claimed or described.

The terms "include," "includes," and "including," as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "free of" as used herein means that the composition comprises 0% of an ingredient by total weight of the composition, thus no detectable amount of the stated ingredient.

The term "substantially free of" as used herein means less than about 1%, less than about 0.8%, less than about 0.5%, less than about 0.3%, or less than an immaterial amount of the stated ingredient by total weight of the composition.

The term "anhydrous" as used herein, unless otherwise specified, refers to those compositions, phases or materials containing less than about 10%, more preferably less than about 5%, even more preferably less than about 3%, even more preferably zero percent of water, by weight of the composition.

The term "cleansing composition" or "personal care composition for cleansing the skin" as used herein refers to cosmetic compositions intended for topical application to the skin for cleansing.

The term "C13 alkyl sulfate anionic surfactant" refers to a sulfated anionic surfactant including an alkyl group having a total number of 13 carbon atom numbers.

The term "2-branched C13 alkyl sulfate anionic surfactant" as used herein refers to a C13 alkyl sulfate anionic surfactant having an alkyl chain positioned at carbon position 2.

The term "Other branched C13 alkyl sulfate anionic surfactant" as used herein refers to any other branched C13 alkyl sulfate anionic surfactants that are not a 2-branched C13 alkyl sulfate anionic surfactant, like 3-branched or 4-branched or 5-branched, etc., C13 alkyl sulfate anionic surfactant. A "Non-C2 branching" means the alkyl chain comprises branching at multiple carbon positions along the alkyl chain backbone, or a single branching group present on a branching position on the alkyl chain other than the C2 position.

The term "mixtures" as used herein is meant to include a simple combination of materials and any compounds that may result from their combination.

The term "package" as used herein includes any suitable container for a personal care composition exhibiting a viscosity from about 1.5 Pa·s (1,500 centipoise (cP)) to about 1 000 Pa·s (1,000,000 cP) as measured by the Viscosity Method as disclosed herein, including but not limited to bottle, tottle, tube, jar, non-aerosol pump and mixtures thereof.

The term "personal care composition" as used herein, refers to compositions intended for topical application to the skin or hair or scalp. The compositions of the present invention are rinse-off formulations, in which the product is applied topically to the skin or hair or scalp and then is subsequently rinsed within minutes from the skin or hair or scalp with water, or otherwise wiped off using a substrate with deposition of a portion of the composition. The compositions also may be used as shaving aids. The personal care composition is typically extrudable or dispensible from a package. The personal care compositions typically exhibit a viscosity of from about 1.5 Pa·s (1,500 centipoise (cP)) to about 1 000 Pa·s (1,000,000 cP) as measured by the T-bar Viscosity Method as disclosed herein. The personal care compositions can be in the form of liquid, semi-liquid, cream, lotion or gel compositions intended for topical application to skin. Examples of personal care compositions can include but are not limited to shampoo, conditioning shampoo, body wash, moisturizing body wash, shower gels, skin cleansers, cleansing milks, hair and body wash, in shower body moisturizer, pet shampoo, shaving preparations and cleansing compositions used in conjunction with a disposable cleansing cloth.

The term "rinse-off" as used herein means the intended product usage includes application to skin or hair or scalp followed by rinsing and/or wiping the product from the skin within a few seconds to minutes of the application step. The product is generally applied and rinsed in the same usage event, for example, a shower.

"Room temperature" refers to a temperature of 25° C.

The term "structured," as used herein means having a rheology that confers stability on the multiphase composition. The degree of structure is determined by characteristics determined by one or more of the following methods: The Young's Modulus Method, or the Zero Shear Viscosity Method or by the Ultracentrifugation Method, all in the Test Methods below. Accordingly, a cleansing phase of the personal care composition is considered "structured," if the surfactant cleansing phase has one or more of the following properties described below according to the Young's Modulus Method, or the Zero Shear Viscosity Method or by the Ultracentrifugation Method. A surfactant phase is considered to be structured, if the phase has one or more of the following characteristics:

A. a Zero Shear Viscosity of at least about 100 Pascal-seconds (Pa-s), alternatively at least about 200 Pa-s, alternatively at least about 500 Pa-s, alternatively at least about 1,000 Pa-s, alternatively at least about 1,500 Pa-s, alternatively at least about 2,500 Pa-s, alternatively at least about 5,000 Pa-s; or B. a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%; or most preferably at least about 90%.

C. a Young's Modulus of greater than about 2 Pascal (Pa), more preferably greater than about 10 Pa, even more preferably greater than about 20 Pa, still more preferably greater than about 30 Pa, 40 Pa, 50 Pa, 75 Pa, 100 Pa, most preferably greater than 150 Pa.

The term "SLS" as used herein, means sodium lauryl sulfate.

The term "lather" as used herein, means the aerated foam which results from providing energy to aqueous surfactant mixtures, especially dilute mixtures. Lather is increased in micellar compositions compared to structured, e.g., lamellar compositions, so that a phase change during dilution to micelles typically increases lather.

The term "visually distinct" as used herein, refers to a region of the personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase can also be constituted or re-constituted, collected, or separated into a bulk phase in order to observe its properties, e.g., by centrifugation, filtration or the like.

The objects of the present invention are to provide personal care products, methods and uses of the products, the structures and the respective compositions as described in the Summary or as described hereinbelow for fulfilling the technical effects or goals as set out herein. These objects and other advantages as may be apparent to those skilled in the art can be achieved through the present invention, which is described in the above Summary of the Invention and Detailed Description of the invention and which is defined in the claims which follow.

Benefits

Chemical contaminants are sometimes found in raw materials or products utilizing raw materials. For example, 1,4-dioxane is an undesirable byproduct of detergent making. As an industrial processing solvent or chemical intermediate, 1,4-dioxane has previously been reported to be used in the production of products that may have commercial or consumer applications such as paints, adhesives, detergents, and pesticides. As such 1,4-dioxane may be present as a contaminant in consumer cosmetics/toiletries, household detergents, pharmaceuticals, foods, agricultural and veterinary products and ethylene glycol-based antifreeze coolants. It is formed as a reaction byproduct during the manufacturing of ethoxylated surfactants. Manufacturers can remove most of the 1,4-dioxane in consumer products through a vacuum stripping process or by improved methods of removing contaminants, like 1,4-dioxane from already ethoxylated surfactants.

However, there is a desire to make personal care compositions that contain relatively very low amount or no ethoxylated surfactants, without having negative consumer noticeable trade-offs.

Initially, a non-ethoxylated surfactant, namely non-ethoxylated sodium tridecyl sulfate (STOS) has been considered as sodium isotridecyl sulfate (Comp. Ex. 1). However, the personal care compositions did not appear to meet the structure and/or stability properties in terms of rheology or did not provide any significant structured attributes to drive any cleansing and any cosmetic attributes sought by the consumer onto skin. The personal care compositions comprising non-ethoxylated sodium tridecyl sulfate did not form lamellar phase.

To provide a personal care composition for cleansing the skin with an improved structure, an improved stability, with an optimum rheology profile, and any attributes sought by the consumer such as lather performance, mildness, etc., a specific surfactant structure needs to be found and optimized. Previously, the surfactant structure included the branched alkyl hydrocarbon chains, a hydrophilic ethoxylate spacer, and an anionic sulfate head group in combination with other ingredient components to produce personal care compositions that organize into a lamellar phase that is desirable for dispensing rheology and aesthetic.

The sodium trideceth-n hydrocarbon is a highly branched alkyl sulfate, and able to accomplish all these structure-related needs for personal care compositions, but in the absence of ethoxylation, inventors have found that it was unable to produce the abundance of multilamellar vesicles necessary to deliver desirable use aesthetics. Further, connected to these structural observations, non-ethoxylated sodium tridecyl sulfate that is highly branched was unable to produce a stable lamellar phase, and does not have the resulting rheological properties for useful product use aesthetics.

Surprisingly, inventors have discovered a new C13 alkyl sulfate anionic surfactant preferably a non-ethoxylated C13 alkyl sulfate anionic surfactant.

The C13 alkyl sulfate anionic surfactant consists of:
(a) less than about 40% by weight of the C13 alkyl sulfate anionic surfactant of a linear C13 alkyl sulfate, and
(b) more than about 60% by weight of the C13 alkyl sulfate anionic surfactant of a 2-branched C13 alkyl sulfate anionic surfactant, wherein the 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight of the 2-branched C13 alkyl sulfate anionic surfactant of 2-methyl dodecyl sulfate anionic surfactant, and
(c) less than about 5% by weight of the C13 alkyl sulfate anionic surfactant of other branched C13 alkyl sulfate anionic surfactant,
wherein (a), (b) and (c) add up to about 100% by weight of the C13 alkyl sulfate anionic surfactant.

Surprisingly, inventors have found by changing the nature and the distribution of the hydrocarbon branching of a 2-branched alkyl sulfate anionic surfactant, personal care compositions comprising the C13 alkyl sulfate anionic surfactant as described herein are structured, stable, with an optimum rheology profile. Also, further attributes sought by the consumer such as enhanced fragrance experience have been found.

Personal Care Composition

A personal care composition is provided and comprises at least a cleansing phase and a benefit phase.

Cleansing Phase

The cleansing phase comprises an aqueous structured surfactant phase. The cleansing phase includes a C13 alkyl sulfate anionic surfactant and a zwitterionic surfactant (as a cosurfactant). Surfactants can help to provide a cleaning benefit, lather properties, and rheology properties to the compositions.

The personal care composition comprises from about 1% to about 20%, preferably from about 2% to about 18%, more preferably from about 3% to about 15%, most preferably from about 4% to about 13% by weight of the composition, of a C13 alkyl sulfate anionic surfactant.

C13 Alkyl Sulfate Anionic Surfactant

The C13 alkyl sulfate anionic surfactant as described herein can be used for personal care compositions selected from the group consisting of personal bar soap, hand soap, shower gels, a shower or bath cream, a foaming body wash, and mixtures thereof.

The C13 alkyl sulfate anionic surfactant consists of: a) less than about 40% by weight of the C13 alkyl sulfate anionic surfactant of a linear C13 alkyl sulfate, b) more than about 60% by weight of the C13 alkyl sulfate anionic surfactant of a 2-branched C13 alkyl sulfate anionic surfactant; and c) less than about 5% by weight of the C13 alkyl sulfate anionic surfactant of other branched C13 alkyl sulfate anionic surfactant, wherein (a), (b) and (c) add up to 100% by weight of the C13 alkyl sulfate anionic surfactant.

The 2-branched C13 alkyl sulfate anionic surfactant comprises: about 25% or less by weight of the 2-branched C13 alkyl sulfate anionic surfactant of 2-pentyl octyl sulfate anionic surfactant, and more than about 25% by weight of the 2-branched C13 alkyl sulfate anionic surfactant of 2-methyl dodecyl sulfate anionic surfactant.

Alternatively, the 2-branched C13 alkyl sulfate anionic surfactant comprises 2-branched alkyl chains: about 25% or less by weight of the 2-branched alkyl chains of 2-pentyl octyl, and more than about 25% by weight of the 2-branched alkyl chains of 2-methyl dodecyl.

By C13 alkyl sulfate anionic surfactant, it is meant that the alkyl sulfate anionic surfactant comprises an alkyl chain which consists of 13 carbon atoms. Thus, for blends of alkyl sulfate anionic surfactant having an average chain length of 13 carbon atoms, only those alkyl sulfate anionic surfactants which comprise a C13 alkyl chain fall under the definition of C13 alkyl sulfate anionic surfactant.

For blends of alkyl sulfate anionic surfactant comprising a mixture of different chain lengths including a C13 alkyl subfraction, independent of the average alkyl chain length, solely this C13 alkyl subfraction falls under the definition of C13 alkyl sulfate anionic surfactant.

With regards to the specific degree and type of C2-branching, the C13 alkyl sulfate anionic surfactant may consist of: a) less than about 30%, preferably from about 5.0% to about 25% by weight of the C13 alkyl sulfate anionic surfactant of the linear C13 alkyl sulfate; b) more than about 70%, preferably from about 75% to about 95% by weight of the C13 alkyl sulfate anionic surfactant of the 2-branched C13 alkyl sulfate anionic surfactant; and c) less than about 3.0%, preferably from about 0.1% to about 2.0% by weight of the C13 alkyl sulfate anionic surfactant of other branched C13 alkyl sulfate anionic surfactant.

The 2-branched C13 alkyl sulfate anionic surfactant may comprise: less than about 20%, preferably from about 5.0% to about 20%, more preferably from about 10% to about 20%, by weight of the 2-branched alkyl chains of 2-pentyl octyl, and more than about 30%, preferably from about 30% to about 50%, more preferably from about 33% to about 50%, by weight of the 2-branched alkyl chains of 2-methyl dodecyl.

Alternatively, the 2-branched C13 alkyl sulfate anionic surfactant may comprise less than about 20%, preferably from about 5.0% to about 20%, more preferably from about 10% to about 20%, by weight of the 2-branched C13 alkyl sulfate anionic surfactant of 2-pentyl-1-octyl sulfate anionic surfactant, and more than about 30%, preferably from about 30% to about 50%, more preferably from about 33% to about 50%, by weight of the 2-branched C13 alkyl sulfate anionic surfactant of 2-methyl-1-dodecyl sulfate anionic surfactant.

Alternatively, the 2-branched C13 alkyl sulfate anionic surfactant may comprise less than about 20%, preferably from about 5.0% to about 20%, more preferably from about 10% to about 20%, by weight of the C13 alkyl sulfate anionic surfactant of 2-pentyl-1-octyl sulfate anionic surfactant, and more than about 28%, preferably from about 28% to about 50%, more preferably from about 29% to about 50%, by weight of the C13 alkyl sulfate anionic surfactant of 2-methyl-1-dodecyl sulfate anionic surfactant.

The remaining fraction within the 2-branched C13 alkyl sulfate anionic surfactant can comprise 2-ethyl-1-undecyl sulfate anionic surfactant (preferably at a level about 25% or less, more preferably about 20% or less, most preferably from about 10% to about 20%, by weight of the 2-branched C13 alkyl sulfate anionic surfactant), 2-propyl-1-decyl sulfate anionic surfactant (preferably at a level about 25% or less, more preferably about 20% or less, most preferably from about 10% to about 18% by weight of the 2-branched C13 alkyl sulfate anionic surfactant) and 2-butyl-1-nonyl sulfate anionic surfactant (preferably at a level about 25% or less, more preferably about 20% or less, most preferably from about 5% to about 18%, by weight of the 2-branched C13 alkyl sulfate anionic surfactant).

Alternatively, the remaining fraction within the 2-branched C13 alkyl sulfate can comprise 2-ethyl-1-undecyl sulfate anionic surfactant (preferably at a level about 25% or less, more preferably about 20% or less, most preferably from about 10% to about 18% by weight of the C13 alkyl sulfate anionic surfactant), 2-propyl-1-decyl sulfate anionic surfactant (preferably at a level about 25% or less, more preferably about 20% or less, most preferably from about 10% to about 15% by weight of the C13 alkyl sulfate anionic surfactant) and 2-butyl-1-nonyl sulfate anionic surfactant (preferably at a level about 25% or less, more preferably about 20% or less, most preferably from about 5% to about 15% by weight of the C13 alkyl sulfate anionic surfactant).

Hence, the distribution of the 2-branched C13 alkyl sulfate with 2-methyl-1-dodecyl sulfate, 2-pentyl-1-octyl sulfate, 2-ethyl-1-undecyl sulfate, 2-propyl-1-decyl sulfate and 2-butyl-1-nonyl sulfate can be provided either by weight of the 2-branched C13 alkyl sulfate anionic surfactant, or by weight of the C13 alkyl sulfate anionic surfactant.

As such, the alkyl chains of the C13 alkyl sulfate anionic surfactant are highly branched, having an increased methyl to pentyl branching ratio compared to other highly branched alcohols such as for example those sold under the Isalchem® trademark which have a much higher pentyl to methyl branching ratio. The average degree of branching is much higher than lower branched alkyl alcohols produced via the OXO process, such as those sold under the Neodol® trademark. Such Neodol® alkyl alcohols have a weight average degree of branching of around 18%.

The personal care composition may be substantially free, or free of alkoxylated anionic sulfate surfactant. Preferably, the personal care composition may be substantially free, or free of ethoxylated anionic sulfate surfactant.

The C13 alkyl sulfate anionic surfactant may be substantially free, or free of alkoxylated anionic sulfate surfactant. In other words, the C13 alkyl sulfate anionic surfactant may have an average degree of alkoxylation of less than 0.5, of less than 0.25, preferably less than 0.1, more preferably the C13 alkyl sulfate anionic surfactant is free of alkoxylation.

Preferably, the C13 alkyl sulfate anionic surfactant may be substantially free, or free of ethoxylated anionic sulfate surfactant. In other words, the C13 alkyl sulfate anionic surfactant may have an average degree of ethoxylation of less than 0.5, of less than 0.25, preferably less than 0.1, more preferably the C13 alkyl sulfate anionic surfactant is free of ethoxylation.

The average degree of alkoxylation is the mol average degree of alkoxylation (i.e., mol average alkoxylation degree) of all the C13 alkyl sulfate anionic surfactant. Hence, when calculating the mol average alkoxylation degree, the moles of C13 non-alkoxylated sulfate anionic surfactant are included:

Mol average alkoxylation degree=($x1$*alkoxylation degree of surfactant 1+$x2$*alkoxylation degree of surfactant 2+ . . . )/($x1$+$x2$+ . . . )

wherein $x1$, $x2$, . . . are the number of moles of each alkyl (or alkoxy) sulfate anionic surfactant of the mixture and alkoxylation degree is the number of alkoxy groups in each alkyl sulfate anionic surfactant.

Suitable alkyl sulfate anionic surfactants can be made using the following process.

A two-step process can be used to produce branched aldehyde products from linear alpha olefin feedstocks, from which the C13 alkyl sulfate anionic surfactants as described herein can be derived. The two-step process uses a rhodium organophosphorus catalyst for both a first process step and a second step. The first step is an isomerization reaction step and the second process step is a hydroformylation reaction step. The branched aldehydes can undergo a further hydrogenation step to produce branched alcohols.

The isomerization and hydroformylation reactions disclosed herein can be catalyzed by a rhodium organophosphorus catalyst which can be at least one of: (1) an organometallic complex of rhodium and one type of an organophosphorus ligand; (2) or an organometallic complex of rhodium and more than one type of an organophosphorus ligand.

The organophosphorous ligand can be a phosphine. In a nonlimiting example of a phosphine ligand, the phosphine ligand can be triphenylphosphine. The organophosphorous ligand can also be a phosphite. In a nonlimiting example of a phosphite ligand, the phosphite ligand can be tris (2,4-di-t-butylphenyl) phosphite. A mixture of organophosphorous ligands of different types can also be used, such as a mixture of a phosphine and a phosphite. In a nonlimiting example of a mixture of organophosphorous ligands, the organophosphorous ligands can be a mixture of triphenylphosphine and tris (2,4-di-t-butylphenyl) phosphite. The reaction system can contain an inert high-boiling solvent, for example a polyalphaolefin. The first catalyst can be formed when the molar ratio of phosphorous to rhodium is in a range of 1:1 to 1000:1, or 5:1 to 50:1, or 15:1 to 25:1. The rhodium concentration can be in a range of 1 ppm to 1000 ppm, or 10 ppm to 200 ppm, or 25 ppm to 75 ppm. The Carbon Monoxide (CO) to Hydrogen ($H_2$) molar ratio can be in a range of 10:1 to 1:10, or 2:1 to 1:2, or 1.3:1 to 1:1.3.

During the isomerization reaction, the first step can be a reaction isomerizing a linear alpha olefin in the presence of Carbon Monoxide (CO) and Hydrogen ($H_2$) at a first pressure. The isomerizing can be catalyzed by the rhodium organophosphorus catalyst which can be at least one of: (1) an organometallic complex of rhodium and one type of an organophosphorus ligand; (2) or an organometallic complex of rhodium and more than one type of an organophosphorus ligand. The isomerization reactions can produce an isomerized olefin comprising linear internal olefins of the same or different types.

The isomerization step can be performed at a temperature in a range of 30° C. to 500° C., or 50° C. to 150° C., or 70°

C. to 100° C. The isomerization step can be performed at a gauge pressure in a range of 0.1 bar (0.01 MPa above atmospheric) to 10 bar (1 MPa above atmospheric), or 0.5 bar (0.05 MPa above atmospheric) to 5 bar (0.5 MPa above atmospheric), or 1 bar (0.1 MPa above atmospheric) to 2 bar (0.2 MPa above atmospheric).

The isomerizing step can produce a reaction product comprising a 20 wt. % or greater isomerized olefin, or a 40 wt. % or greater isomerized olefin, or a 60 wt. % or greater isomerized olefin, or a 90 wt. % or greater isomerized olefin.

During the hydroformylation reaction step, the isomerized olefin is hydroformylated in the presence of CO and $H_2$ at a second pressure higher than the first pressure to produce a branched aldehyde. The hydroformylation reaction can be catalyzed by the rhodium organophosphorus catalyst which can be at least one of: (1) an organometallic complex of rhodium and one type of an organophosphorus ligand; (2) or an organometallic complex of rhodium and more than one type of an organophosphorus ligand. The resultant branched aldehyde is a 2-alkyl branched aldehyde. The linear alpha olefin is 1-dodecene and the branched aldehyde is a branched C13 aldehyde.

The hydroformylating step can be performed at a temperature in a range of 30° C. to 500° C., or 50° C. to 150° C., or 70° C. to 100° C. The hydroformylating step can be performed at a gauge pressure in a range of 5 bar (0.5 MPa above atmospheric) to 400 bar (40 MPa above atmospheric), or 10 bar (1.0 MPa above atmospheric) to 100 bar (10 MPa above atmospheric), or 15 bar (1.5 MPa above atmospheric) to 20 bar (2 MPa above atmospheric).

The hydroformylating step can produce a reaction product comprising a 25 wt. % or greater branched aldehyde, or a 40 wt. % or greater branched aldehyde, or a 60 wt. % or greater branched aldehyde, or a 90 wt. % or greater branched aldehyde.

The products of the hydroformylation reaction can be distilled. The process can have the step of separating the branched aldehyde products resulting from hydroformylation as an overhead product from the first catalyst stream via a distillation process. The distillation step can be performed at a temperature in a range of 100° C. to 200° C., or 125° C. to 175° C. The distillation step can be performed under vacuum at a pressure of less than 500 millibar absolute (0.05 MPa), or less than 100 millibar absolute (0.01 MPa), or less than 30 millibar absolute (0.003 MPa), The process can also have the steps of: hydrogenating the branched aldehyde product in the presence of a hydrogenation catalyst to produce a branched alcohols product composition. The hydrogenating catalyst can be a base metal catalyst, a supported nickel catalyst, a supported cobalt catalyst, a Raney® (W. R. Grace & Co., 7500 Grace Drive, Columbia, MD 21044) nickel catalyst or a precious metal catalyst. The hydrogenating step can be performed at a temperature in a range of 30° C. to 500° C., or 50° C. to 200° C., or 100° C. to 150° C. The hydrogenating step can be performed at a gauge pressure in a range of 5 bar (0.5 MPa above atmospheric) to 400 bar (40 MPa above atmospheric), or 10 bar (1 MPa above atmospheric) to 100 bar (10 MPa above atmospheric), or 30 bar (3 MPa above atmospheric) to 50 bar (5 MPa above atmospheric).

The hydrogenating step can produce a reaction product comprising 25 wt. % or greater branched alcohols, or 40 wt. % or greater branched alcohols, or 60 wt. % or greater branched alcohols, or 90 wt. % or greater branched alcohols.

The C12 olefin source used in the hydroformylation to make the starting C13 aldehydes and subsequent alcohols of use in the present disclosure can have low levels of impurities that lead to impurities in the starting C13 alcohol and therefore also in the C13 alkyl sulfate. While not intending to be limited by theory, such impurities present in the C12 olefin feed can include vinylidene olefins, branched olefins, paraffins, aromatic components, and low levels of olefins having chain-lengths other than 12 carbons. Branched and vinylidene olefins are typically at or below 5% in C12 alpha olefin sources. Impurities in the resulting C13 alcohols can include low levels of linear and branched alcohols in the range of C10 to C16 alcohols, especially C11 and C15 alcohols, typically less than 2% by weight of the mixture, preferably less than 1%; low levels of branching in positions other than the 2-alkyl position resulting from branched and vinylidene olefins are typically less than about 5% by weight of the alcohol mixture, preferably less than 2%; paraffins and olefins, typically less than 1% by weight of the alcohol mixture, preferably less than about 0.5%; low levels of aldehydes with a carbonyl value typically below 500 mg/kg, preferably less than about 200 mg/kg. These impurities in the alcohol can result in low levels of paraffin, linear and branched alkyl sulfates having total carbon numbers other than C13, and alkyl sulfates with branching in positions other than the 2-alkyl location, wherein these branches can vary in length, but are typically linear alkyl chains having from 1 to 6 carbons. The step of hydroformylation can also yield impurities, such as linear and branched paraffins, residual olefin from incomplete hydroformylation, as well as esters, formates, and heavy-ends (dimers, trimers). Impurities that are not reduced to alcohol in the hydrogenation step may be removed during the final purification of the alcohol by distillation.

Alkyl sulfates are typically prepared by the reaction of fatty alcohols with sulfur trioxide ($SO_3$) or its derivatives or by the reaction of unsaturated compounds with sulfuric acid. Processes using sulfur trioxide in particular have gained prominence for fabricating alkyl sulfate anionic surfactants for use in detergent compositions.

Suitable derivatives of sulfur trioxide include sulfur trioxide complexes such as chlorosulfonic acid, sulfuric acid, or sulfamic acid. Sulfur trioxide is preferred since it tends to result in more pure products. The sulfation reaction typically takes place in a continuous process using a cascade, falling film or tube bundle reactor, with the sulfur trioxide being applied in an equimolar or small excess, usually in a temperature range of 20° C. to 60° C., with the reaction temperature being determined at least partially by the solidification point of the fatty alcohol in the reaction. The reaction typically results in the acid form of the C13 alkyl sulfate anionic surfactant which is typically neutralized in a subsequent step, using an alkali such as sodium hydroxide, potassium hydroxide, magnesium hydroxide lithium hydroxide, calcium hydroxide, ammonium hydroxide, monoethanolamine, diethanolamine, triethanolamine, monoisopropanolamine, diamines, polyamines, primary amines, secondary amines, tertiary amines, amine containing surfactants, and mixtures thereof.

Also, it is well known that the process of sulfating fatty alcohols to yield alkyl sulfate anionic surfactants also yields various impurities. The exact nature of these impurities depends on the conditions of sulfation and neutralization. Generally, however, the impurities of the sulfation process include one or more inorganic salts, unreacted fatty alcohol, and olefins ("The Effect of Reaction By-Products on the Viscosities of Sodium Lauryl Sulfate Solutions," Journal of the American Oil Chemists' Society, Vol. 55, No. 12, p. 909-913 (1978), C. F. Putnik and S. E. McGuire). The level of non-alkyl sulfate impurities in the alkyl sulfate anionic surfactant of the present disclosure can be less than 6% by weight, preferably less than 4% by weight, and most preferably less than 2% by weight of the alkyl sulfate anionic surfactant.

For alkyl alkoxy sulfates, the fatty alcohol is first alkoxylated before sulfation. Alkoxylation is a process that reacts lower molecular weight epoxides (oxiranes), such as ethylene oxide, propylene oxide, and butylene oxide with the fatty alcohol. These epoxides are capable of reacting with the fatty alcohol using various base or acid catalysts. In base catalyzed alkoxylation, an alcoholate anion, formed initially by reaction with a catalyst (alkali metal, alkali metal oxide, carbonate, hydroxide, or alkoxide), nucleophilically attacks the epoxide.

Traditional alkaline catalysts for alkoxylation include potassium hydroxide and sodium hydroxide, which give rise to a somewhat broader distribution of alkoxylates. Other catalysts have been developed for alkoxylation that provide a more narrow distribution of alkoxylate oligomers. Suitable examples of narrow range alkoxylation catalysts include many alkaline earth (Mg, Ca, Ba, Sr, etc.) derived catalysts, Lewis acid catalysts, such as Zirconium dodecanoxide sulfate, and certain boron halide catalysts. A specific average degree of alkoxylation may be achieved by selecting the starting quantities of fatty alcohol and ethylene oxide or by blending together varying amounts of alkoxylated surfactants differing from one another in average degree of alkoxylation. The C13 alkyl sulfate anionic surfactant may be a sodium C13 alkyl sulfate anionic surfactant, potassium C13 alkyl sulfate anionic surfactant, triethylammonium C13 alkyl sulfate anionic surfactant, or ammonium C13 alkyl sulfate anionic surfactant.

Additional Anionic Surfactant

The cleansing phase may comprise an additional anionic surfactant. The additional anionic surfactant may be a non-alkoxylated, preferably a non-ethoxylated anionic surfactant.

The additional anionic surfactant may be selected from the group consisting of ammonium lauryl sulfate, ammonium C10-15 alkyl sulfate, ammonium C11-15 alkyl sulfate, ammonium decyl sulfate, ammonium undecyl sulfate, triethylamine lauryl sulfate, triethanolamine lauryl sulfate, monoethanolamine lauryl sulfate, diethanolamine lauryl sulfate, lauric monoglyceride sodium sulfate, sodium lauryl sulfate, sodium C10-15 alkyl sulfate, sodium C11-15 alkyl sulfate, sodium C12-14 alkyl sulfate, sodium decyl sulfate, sodium undecyl sulfate, potassium lauryl sulfate, potassium C10-15 alkyl sulfate, potassium C11-15 alkyl sulfate, potassium C12-14 alkyl sulfate, potassium decyl sulfate, potassium undecyl sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, monoethanolamine cocoyl sulfate, sodium tridecyl benzene sulfonate, sodium dodecyl benzene sulfonate, sodium cocoyl isethionate and mixtures thereof.

Preferably, the additional anionic surfactant may be selected from the group consisting of ammonium lauryl sulfate, ammonium undecyl sulfate, triethylamine lauryl sulfate, triethanolamine lauryl sulfate, monoethanolamine lauryl sulfate, diethanolamine lauryl sulfate, sodium lauryl sulfate, sodium undecyl sulfate, potassium lauryl sulfate, potassium undecyl sulfate, sodium lauroyl sarcosinate, sodium cocoyl isethionate and mixtures thereof.

Most preferred, the additional anionic surfactant may be selected from the group consisting of ammonium lauryl sulfate, triethylamine lauryl sulfate, triethanolamine lauryl sulfate, monoethanolamine lauryl sulfate, diethanolamine lauryl sulfate, sodium lauryl sulfate, potassium lauryl sulfate and mixtures thereof, even most preferred sodium lauryl sulfate.

The cleansing phase may comprise from about 0.5% to about 10%, preferably from about 1% to about 8%, more preferably from about 3% to about 8%, most preferably from about 5% to about 7% by weight of the composition, of an additional anionic surfactant.

Zwitterionic Surfactant

The cleansing phase includes from about 0.1% to about 20%, preferably from about 2% to about 10%, more preferably from about 3% to about 8%, most preferably from about 4% to 7% by weight of the composition, of a zwitterionic surfactant, wherein the zwitterionic surfactant comprises a betaine.

Zwitterionic surfactants suitable for use in the personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate.

The zwitterionic surfactant may comprise an alkyl betaine or an alkyl amidopropyl betaine. Preferably, the zwitterionic surfactant may be selected from the group consisting of cocamidopropyl betaine, coco betaine, and mixtures thereof. More preferably, the zwitterionic surfactant may comprise cocamidopropyl betaine.

When the cleansing phase comprises a C13 alkyl sulfate anionic surfactant and a betaine, the viscosity profile of the cleansing phase and thus of the resulting personal care composition is improved in terms of an increased lamellar phase volume, an enhanced Young's modulus and an increased zero shear viscosity.

The cleansing phase may further comprise an additional cosurfactant may be, for example, an amphoteric surfactant, a nonionic surfactant, or a combination thereof. Suitable amphoteric or zwitterionic surfactants can include those described in U.S. Pat. Nos. 5,104,646 and 5,106,609.

Additional amphoteric detersive surfactants suitable for use in the cleansing phase can include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be 3-(dodecyldimethylammonio)-2-hydroxypropane-1-sulfonate or Lauryl hydroxysultaine, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Nonionic surfactants suitable for use in the personal care compositions can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocamide monoethanolamine, decyl glucoside, or a mixture thereof.

The ratio of the weight percent of C13 alkyl sulfate anionic surfactant to the weight percent of the zwitterionic surfactant may be from about 20:1 to about 4:1, preferably from about 9:1 to about 5:1, more preferably from about 8:1 to about 6:1.

Lamellar Structure

The cleansing phase of the personal care composition comprises an aqueous structured surfactant phase. The cleansing phase is comprised of a structured domain that comprises the surfactants as set out hereinabove. The structured domain may be preferably an opaque structured domain, which is preferably a lamellar phase. The lamellar phase produces a lamellar gel network. The lamellar phase can provide resistance to shear, adequate yield to suspend particles and droplets and at the same time provides long term stability, since it is thermodynamically stable.

The personal care composition may be a structured lamellar composition. The personal care composition may comprise at least a 50% lamellar structure, preferably at least a 60% lamellar structure, more preferably at least a 70% lamellar structure.

Alternatively, the personal care composition may comprise a lamellar phase volume from 50% to 100%, preferably from 60% to 100%, more preferably from 70% to 100% of a lamellar phase volume according to the Ultracentrifugation Method disclosed herein.

Structuring System

The personal care composition includes a structuring system. The structuring system can help to provide structure to the cleansing phase. A structuring system includes an electrolyte. The structuring system may further include a rheology modifier. The structuring system may include a non-ionic emulsifier.

Electrolyte

The structuring system of the personal care composition comprises an electrolyte. The electrolyte may comprise an anion selected from the group consisting of phosphate, chloride, sulfate, citrate, and mixtures thereof; and a cation selected from the group consisting of sodium, ammonium, potassium, magnesium, and mixtures thereof.

The electrolyte may be selected from the group consisting of sodium chloride, ammonium chloride, sodium sulfate, ammonium sulfate, and mixtures thereof. Preferably, the electrolyte may comprise sodium chloride.

The personal care composition comprises from about 0.5% to about 5%, preferably from about 3% to about 5%, more preferably from about 4% to about 4.75%, most preferably from about 4.2% to about 4.75%, by weight of said personal care composition, of the electrolyte.

Rheology Modifier

The structuring system of the cleansing phase comprises from about 0.01% to about 5%, preferably from about 0.1% to about 2%, more preferably from about 0.2% to about 1%, most preferably from about 0.5% to about 1% by weight of the personal care composition, of a rheology modifier.

The rheology modifier may be an associative polymer. Associative polymers are polymers constituted by a hydrophilic main chain and hydrophobic side chains. Their behavior in solution is a result of competition between the hydrophobic and hydrophilic properties of their structure. The hydrophobic units tend to form aggregates constituting linkage points between the macromolecular chains. From a rheological viewpoint, associative water-soluble polymers have a very high viscosifying power in water and retain their viscosity well in a saline medium. In mixed polymer and surfactant systems, surfactant aggregates can form, which are stabilized by different types of interactions: electrostatic interactions, dipolar interactions, or hydrogen bonds. Associative water-soluble polymers can interact more specifically with surfactants due to their hydrophobic portions.

The hydrophilic main chain of these associative polymers can, in particular, result from polymerization of a hydrophilic monomer containing functions onto which hydrophobic chains can subsequently be grafted, for example acid functions. This method of preparing associative polymers is described in particular in the "Water Soluble Polymers", ACS Symposium Series 467, ed. Shalaby W Shalaby et al., Am. Chem. Soc. Washington (1991), pp. 82-200. However, a water-soluble polymer of natural origin, or a natural polymer rendered water-soluble by chemical modification, can also be used. Associative polymers can also be formed by copolymerization of hydrophilic monomers and hydrophobic monomers. These hydrophobic polymers, introduced into the reaction medium in a much smaller quantity than the hydrophilic polymers, generally comprise a fatty hydrocarbon chain. This method of preparation is described in the publication by S. Biggs et. al., J. Phys Chem. (1992, 96. pp 1505-11).

The rheology modifier may be selected from the group consisting of a polyacrylate, a polysaccharide, a modified polyol, an hydrophobically modified polyacrylate, an hydrophobically modified polysaccharide, and mixtures thereof.

The rheology modifier may selected from the group consisting of sodium polyacrylate, acrylates copolymer, Acrylates/Vinyl Isodecanoate Crosspolymer, Acrylates/C10-30 Alkyl Acrylate Crosspolymer, Acrylates/C10-30 alkyl acrylate crosspolymer comprising stearyl side chains with less than about 1% Hydrophobic modification, acrylates/C10-30 alkyl acrylate crosspolymer including octyl side chains with less than about 5% Hydrophobic modification, Ammonium Acryloyldimethyltaurate/Beheneth-25 Methacrylate Crosspolymer, Acrylates/Beheneth-25 Methacrylate Copolymer, Acrylates/Steareth-20 Methacrylate Copolymer, and Acrylates/Steareth-20 Methacrylate Crosspolymer, PEG-150/Decyl Alcohol/SMDI Copolymer, PEG-150/stearyl alcohol/SMDI copolymer, hydroxypropyl starch phosphate, distarch phosphate, sodium carboxymethyl starch, hydroxypropyl starch phosphate, starch, Tapioca starch, xanthan gum, gellan gum, carboxymethyl cellulose, carboxymethyl hydroxyethyl cellulose, hydroxypropyl methyl cellulose, guar gum, hydroxypropyl guar, sodium alginate, and mixtures thereof.

Non-limiting examples of associative polymers being a polyacrylate or an hydrophobically modified polyacrylate include sodium polyacrylate, acrylates copolymer, Acrylates/Vinyl Isodecanoate Crosspolymer (Stabylen 30 from 3V), Acrylates/C10-30 Alkyl Acrylate Crosspolymer (Pemulen TR1 and TR2), Aqupec SER-300 made by Sumitomo Seika of Japan, which is Acrylates/C10-30 alkyl acrylate crosspolymer comprising stearyl side chains with less than about 1% HM, Ammonium Acryloyldimethyltaurate/Beheneth-25 Methacrylate Crosspolymer (Aristoflex HMB from Clariant), Acrylates/Beheneth-25 Methacrylate Copolymer (Aculyn 28 from Rohm and Haas); Acrylates/Steareth-20 Methacrylate Copolymer (Aculyn 22 from Rohm and Haas), and Acrylates/Steareth-20 Methacrylate Crosspolymer (Aculyn 88 from Rohm and Haas).

Acrylate copolymers are defined as polymers of two or more monomers consisting of acrylic acid, methacrylic acid (q.v.) or one of their simple esters. Simple esters of methacrylic acid are made with simple alkyl groups such as methyl, ethyl, propyl and butyl and their respective regioisomers. An example of acrylate copolymers may be Luvimer 100 from BASF which is made of a terpolymer of tert-butyl acrylate, ethyl acrylate and methacrylic acid.

Non-limiting examples of associative polymers being a modified polyol include PEG-150/Decyl Alcohol/SMDI Copolymer (Aculyn 44 from Dow Chemical Company), and PEG-150/stearyl alcohol/SMDI copolymer (Aculyn 46 from Dow Chemical Company).

"SMDI" as used herein means saturated methylene diphenyl diisocyanate. "PEG-150/decyl alcohol/SMDI copolymer" is a copolymer of PEG-150 (q.v.), Decyl Alcohol (q.v.), and Saturated Methylene Diphenyl Diisocyanate (q.v.) (SMDI) monomers. "PEG-150/stearyl alcohol/SMDI copolymer" is a copolymer of PEG-150 (q.v.), Saturated Methylene Diphenyl Diisocyanate (q.v.) (SMDI), and Stearyl Alcohol (q.v.) monomers.

Preferably, the rheology modifier may comprise acrylates/C10-30 alkyl acrylate crosspolymer. Acrylates/C10-30 alkyl acrylate Crosspolymer is a copolymer of C10-30 alkyl acrylate and one or more monomers of acrylic acid, methacrylic acid or one of their simple esters crosslinked with an allyl ether of sucrose or an allyl ether of pentaerythritol.

An exemplary preferred acrylates/C10-30 alkyl acrylate crosspolymer may be Aqupec SER-300 made by Sumitomo Seika of Japan, which is Acrylates/C10-30 alkyl acrylate crosspolymer comprising stearyl side chains with less than about 1% Hydrophobic modification (HM). Other preferred rheology modifiers in that category may comprise stearyl, octyl, decyl and lauryl side chains.

Preferred acrylates/C10-30 alkyl acrylate crosspolymer may be Aqupec SER-150 that is acrylates/C10-30 alkyl acrylates crosspolymer comprising about C18 (stearyl) side chains and about 0.4% HM, and Aqupec HV-701EDR that is acrylates/C10-30 alkyl acrylates crosspolymer which comprises about C8 (octyl) side chains and about 3.5% HM.

The crosslinked rheology modifier may include a percentage hydrophobic modification, which is the mole percentage of monomers expressed as a percentage of the total number of all monomers in the polymer backbone, including both acidic and other non-acidic monomers. The percentage hydrophobic modification of the polymer, hereafter % HM, can be determined by the ratio of monomers added during synthesis, or by analytical techniques such as proton nuclear magnetic resonance (NMR). The alkyl side chain length can be determined similarly.

Non-limiting example of an associative polymer being a polysaccharide or a modified polysaccharide includes starch, Tapioca starch, xanthan gum, gellan gum, carboxymethyl cellulose, carboxymethyl hydroxyethyl cellulose, hydroxypropyl methyl cellulose, guar gum, hydroxypropyl guar, sodium alginate, and mixtures thereof.

The rheology modifier may comprise xanthan gum. Xanthan gum can help to improve the stability of the personal care composition.

Alternatively, the rheology modifier may comprise an hydrophobically modified polysaccharide, especially a modified starch. The modified starch may be selected from the group consisting of hydroxypropyl starch phosphate, distarch phosphate, sodium carboxymethyl starch, and mixtures thereof.

In particular, the modified starch may comprise hydroxypropyl starch phosphate. Hydroxypropyl starch phosphate may be provided as Structure® XL from Nouryon, or C*HiForm™ A12747 from Cargill. Distarch phosphate may be provided as Agenajel 20.306 from Agrana Stärke. Sodium carboxymethyl starch may be provided as Vivastar® CS Instant Powder from J. Rettenmaier & Söhne.

Starch is a carbohydrate polymer consisting of a large number of glucose units linked together primarily by alpha 1-4 glucosidic bonds. The starch polymers come in two forms: linear (amylose) and branched through alpha 1-6 glucosidic bonds (amylopectin), with each glucose unit possessing a maximum of three hydroxyls that can undergo chemical substitution.

Hydroxypropyl starch phosphate is a modified starch. It is obtained in accordance with good manufacturing practice by esterification of food starch with sodium trimetaphosphate or phosphorus oxychloride combined with etherification by propylene oxide. Hydroxypropylation results in substitution of hydroxyl groups with 2-hydroxypropyl ether. In cases of cross-linking, where phosphorus oxychloride, connects two chains, the structure can be represented by: Starch-O—R—O-Starch, where R=cross-linking group and Starch refers to the linear and/or branched structure.

Hydroxypropyl starch phosphate is a naturally-derived and biodegradable rheology modifier that enables more stable and natural emulsions for the personal care application over other rheology modifiers in particular Acrylate/C10-C30 alkyl acrylate crosspolymer. When the rheology modifier is a modified starch, lather has been improved.

Such rheology modifiers or associative polymers can help to provide significant enhancement of structure to the cleansing phase and thus the personal care composition, especially when the personal care composition comprises reduced levels of surfactant; and provide said structure at relatively low levels of rheology modifiers. Also, lather can be further improved.

Not all crosslinked, associative polymers are effective, and many are deleterious to structure. Associative polymers having hydrophobic side chains with fewer than 7 carbons and having % HM greater than about 25% or about 50% are dispreferred.

Non-Ionic Emulsifier

The personal care composition may comprise a non-ionic emulsifier. Preferably the nonionic emulsifier has an HLB from about 3.4 to 13.0, preferably 3.4 to about 8.0.

The personal care composition may comprise a non-ionic emulsifier at concentrations ranging from about 0.1% to about 10%, more preferably from about 0.25% to about 8%, even more preferably from about 0.5% to about 5%, most preferably from about 1.5% to about 2.5%, by weight of the composition.

The balance between the hydrophilic and lipophilic moieties in a surfactant molecule is used as a method of classification (hydrophile-lipophile balance, HLB). The HLB values for commonly-used surfactants are readily available in the literature (e.g., HLB Index in *McCutcheon's Emulsifiers and Detergents*, MC Publishing Co., 2004). Another way of obtaining HLB values is to estimate by calculations. The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20. Other examples of how to calculate HLB values are described by Davies in Interfacial Phenomena, 2nd Edition, Academic Press, London, 1963 and by Lin in *J. Phys. Chem.* 76, 2019-2013, 1972.

The non-ionic emulsifiers for use herein may be selected form the group consisting of glyceryl monohydroxystearate, isosteareth-2, trideceth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Preferably, the non-ionic emulsifiers for use herein may comprise at least one of the following: trideceth-2 and trideceth-3.

The non-ionic emulsifier can help to increase the Young's modulus and thus improve the structure and stability of the personal care composition.

Deposition Polymer

The personal care composition may additionally comprise a cationic deposition polymer in the cleansing phase as a deposition aid for the benefit agents described herein.

Suitable cationic deposition polymers for use in the compositions may contain cationic nitrogen-containing moieties such as quaternary ammonium moieties. Nonlimiting examples of cationic deposition polymers for use in the personal care composition include cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M. Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

The cationic deposition polymers of the personal care composition may have a cationic charge density from about 0.8 meq/g to about 2.0 meq/g, alternatively from about 1.0 meq/g to about 1.5 meq/g.

The personal care composition may comprise from 0.01% to 5%, preferably from 0.1% to 2%, more preferably from 0.2% to 1%, most preferably from 0.3% to 1% by weight of the personal care composition, of a cationic deposition polymer.

Water

The cleansing phase of the personal care composition may comprise water. The cleansing phase of the personal care composition may comprise from about 10% to about 90%, alternatively from about 40% to about 85%, alternatively from about 60% to about 80% by weight water.

Benefit Phase

The personal care composition comprises a benefit phase. The benefit phase in the personal care composition may be hydrophobic or essentially anhydrous and may be substantially free of water. The benefit phase may be substantially free or free of surfactant.

The benefit phase typically comprise a benefit agent. A benefit agent may include water insoluble or hydrophobic benefit agent. The benefit phase may comprise from about 0.1% to about 50%, preferably from about 1% to about 30%, more preferably from about 5% to about 30%, by weight of the personal care composition, of a benefit agent.

The hydrophobic skin benefit agent for use in the benefit phase of the composition may have a Vaughan Solubility Parameter (VSP) of from about 5 to about 15, preferably from about 5 to less than 10. These solubility parameters are well known in the formulation arts, and are defined by Vaughan in Cosmetics and Toiletries, Vol. 103, p 47-69, October 1988.

The benefit agent may be selected from the group consisting of petrolatum; lanolin; derivatives of lanolin; natural waxes; synthetic waxes; volatile organosiloxanes; derivatives of volatile organosiloxanes; non-volatile organosiloxanes; derivatives of non-volatile organosiloxanes; lanolin oil; lanolin esters; natural triglycerides; synthetic triglycerides; and mixtures thereof.

Alternatively, non-limiting examples glycerides suitable for use as hydrophobic skin benefit agents herein include castor oil, soybean oil, derivatized soybean oils such as maleated soybean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, shea butter, and mixtures thereof.

Non-limiting examples of acetoglyceride esters suitable for use as hydrophobic skin benefit agents herein include acetylated monoglycerides.

Non-limiting examples of alkyl esters suitable for use as hydrophobic skin benefit agents herein include isopropyl esters of fatty acids and long chain esters of long chain (i.e. C10-C24) fatty acids, e.g. cetyl ricinoleate, non-limiting examples of which include isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and mixtures thereof.

Non-limiting examples of alkenyl esters suitable for use as hydrophobic skin benefit agents herein include oleyl myristate, oleyl stearate, oleyl oleate, and mixtures thereof.

Non-limiting examples of polyglycerin fatty acid esters suitable for use as hydrophobic skin benefit agents herein include decaglyceryl distearate, decaglyceryl diisostearate, decaglyceryl monomyristate, decaglyceryl monolaurate, hexaglyceryl monooleate, glycerol monooleate glycerol monooleate and mixtures thereof.

Non-limiting examples of lanolin and lanolin derivatives suitable for use as hydrophobic skin benefit agents herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and mixtures thereof.

Non-limiting examples of silicone oils suitable for use as hydrophobic skin benefit agents herein include dimethicone copolyol, dimethylpolysiloxane, diethylpolysiloxane, mixed C1-C30 alkyl polysiloxanes, phenyl dimethicone, dimethiconol, and mixtures thereof. Preferred are non-volatile silicones selected from dimethicone, dimethiconol, mixed C1-C30 alkyl polysiloxane, and mixtures thereof. Nonlimiting examples of silicone oils useful herein are described in U.S. Pat. No. 5,011,681 (Ciotti et al.).

Still other suitable hydrophobic skin benefit agents include milk triglycerides (e.g., hydroxylated milk glyceride) and polyol fatty acid polyesters.

Still other suitable hydrophobic skin benefit agents include wax esters, non-limiting examples of which include beeswax and beeswax derivatives, spermaceti, myristyl myristate, stearyl stearate, and mixtures thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and mixtures thereof. Also suitable benefit agents include glycerol monooleate.

Preferably, the benefit phase may comprise a hydrophobic benefit agent and a lipid bilayer structurant. The lipid bilayer structurant comprises glyceryl monooleate, glyceryl monostearate, glyceryl monolaurate, or a mixture thereof. The benefit agent comprises petrolatum, soybean oil, sucrose polyester, mineral oil, or a mixture thereof.

Physical Contact Between the Cleansing and Benefit Phases

In the personal care composition, the cleansing phase and the benefit phase may be in physical contact. The phases may be blended or mixed to a significant degree, but still be physically distinct such that the physical distinctiveness is undetectable to the naked eye.

The phases can also be made to occupy separate and distinct physical spaces inside a package in which the phases can be stored. In such an arrangement, the structured cleansing phase and the benefit phase can be stored such that the phases are not in direct contact with one another.

Alternatively, the personal care composition may be a multiphase personal care composition where the phases of the personal care composition are made to occupy separate but distinct physical spaces inside the package in which they are stored, but are in direct contact with one another (i.e., they are not separated by a barrier and they are not emulsified or mixed to any significant degree).

The cleaning phase and the benefit phase can be in physical contact while remaining visibly distinct to give, for example, a striped or marbled or geometric configuration.

Optional Ingredients

While not essential for the purposes of the present disclosure, the non-limiting list of materials, in addition to the previously disclosed, optional materials, illustrated hereinafter are suitable for use in the personal care composition, and may be desirably incorporated in certain embodiments, for example to assist or enhance cleansing performance, for treatment of the skin, or to modify the aesthetics of the personal care composition as is the case with perfumes, colorants, dyes or the like. Optional materials useful in the products herein are categorized or described by their cosmetic and/or therapeutic benefit or their postulated mode of action or function. However, it is to be understood that the active and other materials useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed. The precise nature of these optional materials, and levels of incorporation thereof, will depend on the physical form of the composition and the nature of the cleansing operation for which it is to be used. The optional materials are usually formulated at less than about less than about 6%, less than about 5%, less than about 4%, less than about 3%, less than about 2%, less than about 1%, less than about 0.5%, less than about 0.25%, less than about 0.1%, less than about 0.01%, less than about 0.005% of the personal care composition.

The phases of the personal care compositions, preferably the cleansing phase, optionally can further comprise a liquid crystalline phase inducing structurant, which when present is at concentrations ranging from about 0.3% to about 15%, by weight of the phase. Suitable liquid crystalline phase inducing structurants include trihydroxystearin (available from Rheox, Inc. under the trade name THIXCIN® R). The personal care composition is free of fatty acid due to its negative impact on lather performance.

Other non-limiting optional ingredients that can be used in the personal care composition may comprise an optional benefit component that is selected from the group consisting of thickening agents; preservatives; antimicrobials; fragrances; chelators (e.g. such as those described in U.S. Pat. No. 5,487,884 issued to Bisset, et al.); sequestrants; vitamins (e.g. Retinol); vitamin derivatives (e.g. tocophenyl actetate, niacinamide, panthenol); sunscreens; desquamation actives (e.g. such as those described in U.S. Pat. Nos. 5,681,852 and 5,652,228 issued to Bisset); anti-wrinkle/anti-atrophy actives (e.g. N-acetyl derivatives, thiols, hydroxyl acids, phenol); anti-oxidants (e.g. ascorbic acid derivatives, tocophenol) skin soothing agents/skin healing agents (e.g. panthenoic acid derivatives, aloe vera, allantoin); skin lightening agents (e.g. kojic acid, arbutin, ascorbic acid derivatives) skin tanning agents (e.g. dihydroxyacetone); anti-acne medicaments; essential oils; sensates; pigments; colorants; pearlescent agents; interference pigments (e.g. such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g. talc, kaolin, mica, smectite clay, cellulose powder, polysiloxane, silicas, carbonates, titanium dioxide, polyethylene beads) hydrophobically modified non-platelet particles (e.g. hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof.

The personal care composition may comprise from about 0.1% to about 4%, by weight of the personal care composition, of hydrophobically modified titanium dioxide.

One or more of the phases of the personal care composition can comprise a variety of additional optional ingredients such as shiny particles, beads, exfoliating beads. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Methods of Use

The personal care compositions may be preferably applied topically to the desired area of the skin or hair in an amount sufficient to provide effective delivery of the skin cleansing agent, hydrophobic material, and particles to the applied surface. The compositions can be applied directly to the skin or indirectly via the use of a cleansing puff, washcloth, sponge or other implement. The compositions may be preferably diluted with water prior to, during, or after topical application, and then subsequently the skin or hair rinsed or wiped off, preferably rinsed off of the applied surface using water or a water-insoluble substrate in combination with water. The present disclosure is therefore also directed to methods of cleansing the skin through the above-described application of the compositions.

A method of increasing stability of a personal care composition is provided and comprises the step of forming a personal care composition as set out hereinbefore with a C13 alkyl sulfate anionic surfactant, wherein the C13 alkyl sulfate anionic surfactant consists of:
  (a) less than about 40% by weight of the C13 alkyl sulfate anionic surfactant of a linear C13 alkyl sulfate, and
  (b) more than about 60% by weight of the C13 alkyl sulfate anionic surfactant of a 2-branched C13 alkyl sulfate anionic surfactant, wherein the 2-branched C13 alkyl sulfate anionic surfactant comprises:
    about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and
(c) less than about 5% by weight of the C13 alkyl sulfate anionic surfactant of other branched C13 alkyl sulfate anionic surfactant, wherein a, b and c add up to about 100% by weight of the C13 alkyl sulfate anionic surfactant.

A method of enhancing deposition of a benefit agent of a personal care composition is provided and comprises, preferably in that order, the step of forming a personal care composition as set out hereinbefore with a C13 alkyl sulfate anionic surfactant, wherein the C13 alkyl sulfate anionic surfactant consists of:
  (a) less than about 40% by weight of the C13 alkyl sulfate anionic surfactant of a linear C13 alkyl sulfate, and
  (b) more than about 60% by weight of the C13 alkyl sulfate anionic surfactant of a 2-branched C13 alkyl sulfate anionic surfactant, wherein the 2-branched C13 alkyl sulfate anionic surfactant comprises:
    about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and
  (c) less than about 5% by weight of the C13 alkyl sulfate anionic surfactant of other branched C13 alkyl sulfate anionic surfactant, wherein a, b and c add up to about 100% by weight of the C13 alkyl sulfate anionic surfactant; and the step of placing the personal care composition onto the skin and/or hair of a consumer.

A method of enhancing hydration or perfume scent of the skin and/or hair of a consumer is provided and comprises, preferably in that order, the step of forming a personal care composition as set out hereinbefore with a C13 alkyl sulfate anionic surfactant, wherein the C13 alkyl sulfate anionic surfactant consists of:
  (a) less than about 40% by weight of the C13 alkyl sulfate anionic surfactant of a linear C13 alkyl sulfate, and
  (b) more than about 60% by weight of the C13 alkyl sulfate anionic surfactant of a 2-branched C13 alkyl sulfate anionic surfactant, wherein the 2-branched C13 alkyl sulfate anionic surfactant comprises:
    about 25% or less by weight of the 2-branched C13 alkyl sulfate anionic surfactant of 2-pentyl octyl sulfate anionic surfactant, and more than about 25% by weight the 2-branched C13 alkyl sulfate anionic surfactant of 2-methyl dodecyl sulfate anionic surfactant; and
  (c) less than about 5% by weight of the C13 alkyl sulfate anionic surfactant of other branched C13 alkyl sulfate anionic surfactant, wherein a, b and c add up to about 100% by weight of the C13 alkyl sulfate anionic surfactant; and the step of placing the personal care composition onto the skin and/or hair of the consumer.

Use of a C13 alkyl sulfate anionic surfactant for providing a structured or improved stable personal care composition, as described hereinbefore.

Use of a C13 alkyl sulfate anionic surfactant for providing an improved lather performance of a personal care composition, as described hereinbefore.

Use of a C13 alkyl sulfate anionic surfactant for providing mildness of a personal care composition, as described hereinbefore.

Use of a C13 alkyl sulfate anionic surfactant for enhancing fragrance experience of a personal care composition, as described hereinbefore. Enhancing fragrance experience can mean Leaving a pleasant and/or long-lasting scent onto the skin and/or hair.

Method of Manufacturing

The personal care compositions may be prepared by any known or otherwise effective technique, suitable for making and formulating the desired product form. It is also effective to combine toothpaste-tube filling technology with a spinning stage design. Additionally, the personal care composition may be prepared by the method and apparatus as disclosed in U.S. Pat. No. 6,213,166 issued to Thibiant, et al. The method and apparatus allows two or more compositions to be filled in a spiral configuration into a single container using at least two nozzles which fill the container, which is placed on a static mixer and spun as the composition is introduced into the container.

Alternatively, the personal care composition may be prepared by a method disclosed in commonly owned patent application published on Nov. 18, 2004 under U.S. Publication No. 2004/0219119 A1 entitled "Visually distinctive multiple liquid phase compositions" filed by Wei, et al. on Apr. 30, 2004. The method and apparatus allows two separate compositions to be combined in predetermined amounts, blended into a single resultant composition with visually distinct phases, and filled by one nozzle into a single container that is lowered and rotated during filling.

If the personal care compositions are patterned, it can be desirable to be packaged as a personal care article. The personal care article would comprise these compositions in a transparent or translucent package such that the consumer can view the pattern through the package. Because of the viscosity of the subject compositions it may also be desirable to include instructions to the consumer to store the package upside down, on its cap to facilitate dispensing.

Packaging

Personal care compositions can be dispensed from a squeezable package with an orifice, such as a conventional body wash or shampoo package. The package can be a compact package, i.e., contain less than about 250 ml, or 200 ml, or 150 ml of volume to signal the contents are concentrated. The shear thinning compositions can be dispensed from a package with a slit valve orifice or other flexible orifice, which is generally cut from a silicone elastomeric material and inserted into an orifice housing.

When the composition has a relatively low viscosity, preferably less than about 0.25 Pa·s, at 10 1/sec, it can be dispensed from a foaming package such as a pump foamer. Compositions can also be dispensed from liquid pump packages.

Test Methods

It is understood that the test methods that are disclosed in the Test Methods Section of the present application should be used to determine the respective values of the parameters of Applicants' invention as such invention is described and claimed herein.

T-Bar Viscosity Method

The viscosity of a personal care composition can be assessed by the T-Bar Viscosity Method. The apparatus for T-Bar measurements includes a Brookfield DV-II+ Pro Viscometer with Helipath Accessory; a chuck, weight and closer assembly for T-bar attachment; a T-bar Spindle D, a personal computer with Rheocalc software from Brookfield, and a cable connecting a Brookfield Viscometer to a computer. First, weigh 80 grams of a personal care composition in a 4-oz. glass jar. Measure a T-bar viscosity by carefully dropping the T-Bar Spindle to an interior bottom of the glass jar and set the Helipath stand to travel in an upward direction. Open the Rheocalc software and set the following data acquisition parameters: Speed to 5 rpm, Time Wait for Torque to 00:01 (1 second), and Loop Start Count to 100. Start data acquisition and turn on the Helipath stand to travel upward at a speed of 22 mm/minute. The T-Bar viscosity is an average T-Bar viscosity reading between the $10^{th}$ reading and the $90^{th}$ reading (the first ten readings and the last ten readings are not used for the average T-Bar viscosity calculation). The T-Bar viscosity reading is provided in cP (1 cP is equal to 1 mPa·s). After obtaining the initial viscosity reading, place the personal care composition at 50° C. for 10 days for rapid aging. After finishing the stability testing at 50° C., the sample is equilibrated at 25° C. for 24 hours. Then repeat viscosity measurement to obtain final viscosity. Measure percent change of the initial viscosity from the final viscosity measurement to obtain the percent change in viscosity.

Zero Shear Viscosity and Young's Modulus Methods

The Zero Shear Viscosity of a material which is a phase or a composition of the personal care composition, can be measured either prior to combining in the composition, after preparing a composition, or first separating a phase or component from a composition by suitable physical separation means, such as centrifugation, pipetting, cutting away mechanically, rinsing, filtering, or other separation means.

A controlled stress rheometer such as a TA Instruments Discovery HR2 Rheometer is used to determine the Zero Shear Viscosity. The determination is performed at 25° C. with the 4 cm diameter parallel plate measuring system and a 1 mm gap. The geometry has a shear stress factor of 79580 $m^{-3}$ to convert torque obtained to stress. Serrated plates can be used to obtain consistent results when slip occurs.

First the material (i.e. the sample to be tested) is positioned on the rheometer base plate, the measurement geometry (upper plate) is moved into position 1.1 mm above the base plate. Excess material at the geometry edge is removed by scraping after locking the geometry. The geometry is then moved to the target 1 mm position above the base plate and a pause of about 1 minute is allowed to allow loading stresses to relax. This loading procedure ensures no tangential stresses are loaded at the measurement onset, which can influence results obtained. If the material comprises particles discernible to the eye or by feel (beads, e.g.) which are larger than about 150 microns in number average diameter, the gap setting between the base plate and upper plate is increased to the smaller of 4 mm or 8-fold the diameter of the 95th volume percentile particle diameter. If a phase has any particle larger than 5 mm in any dimension, the particles are removed prior to the measurement.

The measurement is performed by applying a continuous shear stress ramp from 0.1 Pa to 1,000 Pa over a time interval of 4 minutes using a logarithmic progression, i.e., measurement points evenly spaced on a logarithmic scale. Thirty (30) measurement points per decade of stress increase are obtained. If the measurement result is incomplete, for example if material is observed to flow from the gap, results obtained are evaluated with incomplete data points excluded. If there are insufficient points to obtain an accurate measurement, the measurement is repeated with increased number of sample points.

The Young's Modulus (Pa) is obtained by graphing the Stress (Pa) vs. Strain (unitless) and obtaining the slope of the regression line of the initial linear region between Stress vs. Strain, typically occurring in the region below about 4% strain. If the relationship is not linear, the linear regression line slope below 2% strain is taken as the Young's Modulus (Pa), using unitless strain.

The Zero Shear Viscosity is obtained by taking a first median value of viscosity in Pascal-seconds (Pa-sec) for viscosity data obtained between and including 0.1 Pa and the point where viscosity begins to steeply decline. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

The personal care composition may have a Zero Shear Viscosity of at least about 1,000 Pa-s, alternatively at least about 1,500 Pa-s, alternatively at least about 2,500 Pa-s, alternatively at least about 5,000 Pa-s.

The personal care composition may have a Young's Modulus of at least about 40 Pa, alternatively at least about 50 Pa, alternatively at least about 75 Pa, alternatively at least about 100 Pa, alternatively at least about 150 Pa.

Ultracentrifugation Method

The Ultracentrifugation Method is used to determine the percent of a structured domain or an opaque structured domain (e.g., a lamellar phase) that is present in a multiphase personal care composition. The method involves the separation of the composition by ultracentrifugation into separate but distinguishable layers. The multiphase personal care composition of the present invention can have multiple distinguishable layers (e.g. a structured surfactant layer, and a benefit layer).

A composition is separated by ultracentrifuge into separate but distinguishable layers. The multiphase personal care composition of the present invention can have multiple distinguishable layers (e.g., a structured surfactant layer, and a benefit layer).

First, dispense about 4 grams of composition into a Beckman Centrifuge Tube (11×60 mm) to fill the tube. Place the centrifuge tubes in an ultracentrifuge (Beckman Model L8-M or equivalent) using a sling rotor and ultracentrifuge using the following conditions: 50,000 rpm, 2 hours, and 40° C.

Measure the relative phase volumes of the phases the composition by measuring the height of each layer using an Electronic Digital Caliper (within 0.01 mm). Layers are identified by those skilled in the art by physical observation techniques paired with chemical identification if needed. For example, the structured surfactant layer is identified by transmission electron microscopically (TEM), polarized light microscopy, and/or X-ray diffraction for the present invention as a structured lamellar phase comprising multi-lamellar vesicles, and the hydrophobic benefit layer is identified by its low moisture content (less than 10% water as measured by Karl Fischer Titration). The total height $H_a$ is measured which includes all materials in the ultracentrifuge tube. Next, the height of each layer is measured from the bottom of the centrifuge tube to the top of the layer, and the span of each layer algebraically determined by subtraction. The benefit layer may comprise several layers if the benefit phase has more than one component which may phase splits into liquid and waxy layers, or if there is more than one benefit component. If the benefit phase splits, the sum of the benefit layers measured is the benefit layer height, $H_b$. Generally, a hydrophobic benefit layer when present, is at the top of the centrifuge tube.

The cleansing phase may comprise several layers or a single layer, $H_c$. There may also be a micellar, unstructured, clear isotropic layer at the bottom or next to the bottom of the ultracentrifuge tube. The layers immediately above the isotropic phase generally comprise higher surfactant concentration with higher ordered structures (such as liquid crystals). These structured layers are sometimes opaque to naked eyes, or translucent, or clear. There may be several structured layers present, in which case $H_c$ is the sum of the individual structured layers. If any type of polymer-surfactant phase is present, it is considered a structured phase and included in the measurement of $H_c$. The sum of the aqueous phases is $H_s$.

Finally, the structured domain volume ratio is calculated as follows:

Structured Domain Volume Ratio=$H_c/H_s*100\%$

If there is no benefit phase present, use the total height as the surfactant layer height, $H_s=H_a$. For the present invention, the Structured Domain Volume Ratio is the Lamellar Phase %.

The personal care composition may have a Structured Domain Volume Ratio of at least about 40%, alternatively at least about 45%, alternatively at least about 50%, alternatively at least about 55%, alternatively at least about 60%, alternatively at least about 65%, alternatively at least about 70%, alternatively at least about 75%, alternatively at least about 80%, alternatively at least about 85%, and alternatively greater than about 90% by volume of the aqueous structured surfactant phase.

Third-Phase Method for Determining Structured Surfactant Stability

The "Third-Phase" Method is used to determine structured surfactant phase stability in a personal care composition. The method involves placing the personal care compositions at 50° C. for 10 days for rapid aging. After rapid aging, transfer about 4 grams of the composition into a Beckman Centrifuge Tube (11×60 mm). Place the centrifuge tube in a Beckman LE-80 Ultracentrifuge and operate the Ultracentrifuge under the following conditions: 50,000 rpm, 2 hours, and at 40° C.

Figure 3:
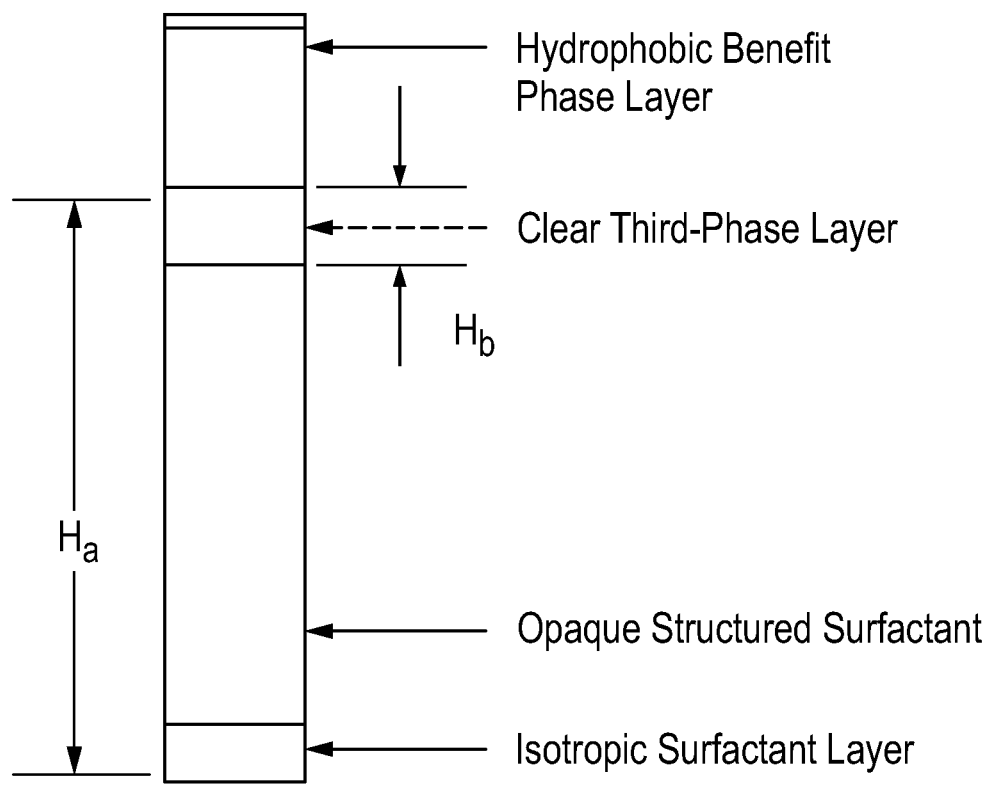
FIG. 3 is an illustration for determining the third-phase volume.

After Ultracentrifugation, determine the third-phase volume by measuring the height of various surfactant phases using an Electronic Digital Caliper (within 0.01 mm) as illustrated in FIG. 3 An example is shown in FIG. 3 for a personal care composition comprising Expancel microsphere.

The very top layer is an hydrophobic benefit phase layer (hydrocarbons or soybean oil etc.). The layers below the hydrophobic benefit phase layers contain surfactant/water are determined in the following: $H_a$ is the height of all layers containing surfactant/water and $H_b$ is the height of the clear "third-phase" layer just below the hydrophobic benefit phase layer. It is important to record the readings within 30 mins after the Ultracentrifugation is finished to minimize material migration across different layers. The third phase volume is calculated as:

Third-phase Volume %=$H_b/H_a*100\%$

Preferably, the aqueous structured surfactant phase or composition may comprise less than 10% "third-phase" volume after rapid aging stability protocol. More preferably, the aqueous structured surfactant phase or composition may comprise less than 5% "third-phase" volume after rapid aging stability protocol. More preferably, the aqueous structured surfactant phase or composition may comprise less than 2% "third-phase" volume after rapid aging stability protocol. Even more preferably, the aqueous structured surfactant phase or composition may comprise less than 1% "third-phase" volume after rapid aging protocol. Most preferably, the aqueous structured surfactant phase or composition may comprise about 0% "third-phase" volume after rapid aging protocol.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Examples of Suitable Alkyl Sulfate Anionic Surfactants and their Synthesis

The following are representative and non-limiting examples of suitable C13 alkyl sulfate anionic surfactants, including a non-limiting method of synthesis.

Using the above-described processes, the alcohol compositions described below in Alcohol Example 1 are obtained and analyzed by gas chromatography with flame ionization detection (GC/FID). The samples are prepared as a 1% (w/v) dichloromethane solution and injected into a capillary GC Column: DB-1 HT 15 m×0.25 mm ID, 0.1 µm film thickness, using an oven temperature program [initial temperature 80° C. (1 min), ramp 10° C./min to 220° C., ramp 30° C./min to 350° C. (1 min)] for a total run time of 19 minutes. Additional GC parameters include Column Flow: 1.4 ml/min ($H_2$), Injection Temperature: 300° C., Sample Amount: 1 µL, Split Ratio: 1/400, FID Temperature: 350° C., $H_2$ Flow: 40 mL/min, Air Flow: 400 mL/min, and Makeup Gas Flow: 25 mL/min.

Alcohol Example 1. Synthesis of Narrow Branched Tridecanol (Alcohol 1)

A C12 linear alpha olefin feedstock (1-Dodecene) was obtained from the Chevron Phillips Chemical Company LP, as identified by product name AlphaPlus® 1-Dodecene (Chevron Phillips Chemical Company LP, P.O. Box 4910, The Woodlands, TX 77387-4910, US, phone (800) 231-3260). The homogeneous rhodium organophosphorus catalyst used in this example is prepared in a high pressure, stainless steel stirred autoclave. To the autoclave was added 0.027 wt. % Rh(CO)2ACAC ((Acetylacetonato)dicarbonylrhodium(I)), 1.36 wt. % tris (2,4,-di-t-butylphenyl) phosphite ligand and 98.62 wt. % Synfluid® PAO 4 cSt (Chevron Phillips Chemical Company LP, P.O. Box 4910, The Woodlands, TX 77387-4910) inert solvent. The mixture was heated at 80° C. in the presence of a $CO/H_2$ atmosphere and 2 bar (0.2 MPa above atmospheric) gauge pressure for four hours to produce the active rhodium catalyst solution (109 ppm rhodium, P:Rh molar ratio=20). The 1-Dodecene linear alpha olefin was added to the rhodium catalyst solution in the autoclave producing a starting reaction mixture with a rhodium concentration of 35 ppm. The alpha olefin feed was then isomerized at 80° C. in the presence of a $CO/H_2$ atmosphere and 1 bar (0.1 MPa above atmospheric) gauge pressure for 10 hours. The isomerized olefin was then hydroformylated at 70° C. in the presence of a $CO/H_2$ atmosphere and 20 bar (2 MPa above atmospheric) gauge pressure for 8 hours. The molar ratio of CO to $H_2$ in both the isomerization step and the hydroformylation step was equal to 1:1.15. The resulting hydroformylation reaction product was flash distilled at 140-150° C. and 25 millibar to recover the rhodium catalyst solution as a bottoms product and recover a branched C13 Aldehyde overheads product with a composition comprising:

| | |
|---|---|
| 1-Tridecanal | 13.9 wt. % |
| 2-Methyl-dodecanal | 28.3 wt. % |
| 2-Ethyl-undecanal | 15.2 wt. % |
| 2-Propyl-decanal | 14.5 wt. % |
| 2-Butyl-nonanal | 13.6 wt. % |
| 2-Pentyl-octanal | 12.6 wt. % |
| Other | 1.9 wt. % |

The weight % branching in the branched C13 aldehyde product was 86.2%.

The branched C13 aldehyde product was hydrogenated in a high pressure, Inconel 625 stirred autoclave at 150° C. and 20 bar (2 MPa above atmospheric) hydrogen gauge pressure. The hydrogenation catalyst used was a Raney® Nickel 3111 (W. R. Grace & Co., 7500 Grace Drive, Columbia, MD 21044, US, phone 1-410-531-4000) catalyst used at a 0.25 wt. % loading. The aldehyde was hydrogenated for 10 hours and the resultant reaction mixture was filtered to produce a branched C13 alcohol product (Alcohol 1 in Table 1) comprising:

| | |
|---|---|
| 1-Tridecanol | 13.36 wt. % |
| 2-Methyl-dodecanol | 28.95 wt. % |
| 2-Ethyl-undecanol | 16.25 wt. % |
| 2-Propyl-decanol | 13.92 wt. % |
| 2-Butyl-nonanol | 13.46 wt. % |
| 2-Pentyl-octanol | 13.02 wt. % |
| Other | 1.04 wt. % |

The weight % 2-alkyl branching in the branched C13 alcohol product was 85.6%.

Alkyl Sulfate Example 1. Synthesis of Narrow Branched Tridecanol Sulfate Using a Falling Film Sulfation Reactor The alcohol from Alcohol Example 1 is sulfated in a falling film using a Chemithon single 15 mm×2 m tube reactor using $SO_3$ generated from a sulfur burning gas plant operating at 2.5 kg/h (5.5 lb/hr) sulfur to produce 3.76% $SO_3$ on a volume basis. Alcohol feed rate is 15.2 kg/hour and feed temperature was 27.2° C. (81° F.). Conversion of the alcohol to alcohol sulfate acid mix was achieved with 96.5% completeness. Neutralization with 50% sodium hydroxide is completed at ambient process temperature to 0.65% excess sodium hydroxide. 33 gallons of sodium neutralized C13 narrow branched Alcohol Sulfate paste. Analyses by standard Cationic $SO_3$ titration method determines final average product activity to be 73.4%. The average unsulfated level is 2.10% w/w.

Alkyl Sulfate Example 2. Synthesis of Narrow Branched Tridecanol Sulfate Using a Falling Film Sulfation Reactor with Amine Oxide Addition The alcohol from Alcohol Example 1 is sulfated in a falling film using a Chemithon single 15 mm×2 m tube reactor using $SO_3$ generated from a sulfur burning gas plant operating at 2.3 kg/h (5.0 lb/hr) sulfur to produce 3.76% $SO_3$ on a volume basis. Alcohol feed rate is 13.8 kg/hour and feed temperature was 23.9° C. (75° F.). Conversion of the alcohol to alcohol sulfate acid mix was achieved with 97% completeness. Neutralization is co-neutralized with 50% sodium hydroxide and with C12/14 dimethyl amine oxide at ambient process temperature to a pH of 8.0. 68 kilograms of the C13 narrow branched Alcohol Sulfate/Amine oxide paste was made to a target activity of 51.7% Alcohol sulfate and 11.76% C12/14 dimethyl amine oxide.

The effect of type of branching within the alkyl chain of the C13 alkyl sulfate anionic surfactants was evaluated for performance within personal care formulations in terms of gel stability, structured features, lather stability, miscibility and perfume benefits, following the test methods described hereinabove.

Test Materials:

The relative performance was determined for C13 alkyl sulfate anionic surfactants based on the starting alcohol summarized in Table 1. The starting alcohol ex table 1 consisted essentially of C13 alkyl chains. Alcohol 1 used to make the C13 alkyl sulfate anionic surfactants in the inventive composition has a type of branching as described in the claims and were produced following the making process described herein.

TABLE 1

Alkyl chain distribution of starting C13 alcohols

| | Alcohol 1 from Alcohol Example 1 |
|---|---|
| Alkyl chain length | C13 |
| Linear content[+] | 13.4% |
| 2-Alkyl Branched C13 Alcohol[+] | 85.6% |
| Other[+++] | 1.0% |
| 2-methyl-1-dodecanol[+] | 29.0 |
| 2-ethyl-1-undecanol[+] | 16.2 |
| 2-propyl-1-decanol[+] | 13.9 |
| 2-butyl-1-nonanol[+] | 13.5 |
| 2-pentyl-1-octanol[+] | 13.0 |
| 2-Alkyl Branch distribution: | |
| 2-methyl-1-dodecanol[++] | 33.9% |
| 2-ethyl-1-undecanol[++] | 18.9% |
| 2-propyl-1-decanol[++] | 16.2% |
| 2-butyl-1-nonanol[++] | 15.8% |
| 2-pentyl-1-octanol[++] | 15.2% |

[+]by weight of starting C13 alcohol
[++]by weight of branched C13 alcohol
[+++]such as isomers with branches in non-C2 positions, paraffins, alcohols with chainlengths other than 13 carbons The starting C13 alcohol of Table 1 was individually sulfated in the pilot plant according to one of the processes as set out above. The resulting alkyl sulfate distribution is retained and corresponds to the distribution of the alkyl chains as set out for the Alcohol 1 in Table 1.

Surfactant Composition Comparisons

The surfactant compositions of Table 1 (below) were prepared by adding water in a mixing vessel. Then add the following ingredients with continuously mixing: sodium lauroamphoacetate or cocamidopropyl betaine, the anionic surfactant, trideceth-3, EDTA, sodium benzoate, and sodium chloride. Adjust pH by adding citric acid solution (50% active) to pH=5.7±0.2. Then, add Methylchloroisothiazolinone and methyl isothiazolinone. Keep mixing until homogeneous.

After preparing these compositions, their Lamellar Phase Volume, Young's Modulus, and Zero Shear Viscosity were determined utilizing the methods disclosed herein. The results are captured below in Table I, as well as graphically in FIG. 1. FIG. 1 displays the rheology profile as a function of shear stress of inventive and comparative examples.

Stability is typically assessed by measuring the Lamellar Phase Volume through the Ultracentrifugation Method as set out hereinbefore, after aging the products at 50° C. for 10 days.

Comparative Example 1 comprises as the anionic surfactant, sodium isotridecyl sulfate which comprises a mixture of branched chain 13 carbon aliphatic alkyl sulfates. Comparative Example 1 was not structured and not stable at all with no lamellar phase volume and a relatively low Young's modulus and Zero Shear Viscosity.

However, when sodium isotridecyl sulfate has been replaced by a C13 alkyl sulfate anionic surfactant as described herein like sodium C13 Alkyl sulfate anionic surfactant obtained from Alcohol 1 (Comparative Example 2), a significant improvement of the viscosity profile of the surfactant phase composition has been observed with a significant increase of both Young's modulus and Zero Shear Viscosity.

Also, in addition, when the amphoteric surfactant sodium lauroamphoacetate has been substituted by cocamidopropyl betaine as the zwitterionic surfactant, a further significant increase in the of both Young's modulus and Zero Shear Viscosity has been obtained. Example 1 with a maintained 100% Lamellar Phase Volume was structured and stable; and has an improved viscosity profile, showing the effectiveness of combining a C13 alkyl sulfate anionic surfactant as recited herein with a zwitterionic surfactant comprising a betaine to drive the lamellar phase formation.

After preparing these compositions, their Lamellar Phase Volume, Young's Modulus, and Zero Shear Viscosity were determined utilizing the methods disclosed herein. The results are captured below in Table II.

The aqueous structured surfactant phase composition may also include an additional anionic surfactant such as sodium lauryl sulfate in order to reduce the level of the C13 alkyl sulfate anionic surfactant while increasing the total level of lathering surfactants without impacting the stability and the structure of the surfactant phase composition as shown in Example 3. Increasing the total level of lathering surfactants can help to enhance lather performance.

When comparing Example 3 to Comparative Example 3 which is a reference surfactant composition comprising sodium trideceth-2 sulfate, the replacement with sodium C13 Alkyl sulfate anionic surfactant obtained from Alcohol 1 has shown still a significant slight increase of the viscosity profile in terms of both Young's modulus and Zero Shear Viscosity. Again, the data shows that the effectiveness of using in the cleansing phase a C13 Alkyl sulfate anionic surfactant.

Also, Example 3 shows that a blend of a C13 Alkyl sulfate anionic surfactant and sodium lauryl sulfate can help to improve the rheology profile of the aqueous structured surfactant phase or composition.

When comparing Example 3 to Example 2, the inclusion of sodium lauryl sulfate with a lower level of sodium C13 Alkyl sulfate anionic surfactant obtained from Alcohol 1, while increasing the total level of lathering surfactants in Example 3, has shown still a significant increase of the viscosity profile in terms of both Young's modulus and Zero Shear Viscosity.

TABLE I

| Surfactant Phase Composition | Comparative Example 1 (w/w %) | Comparative Example 2 (w/w %) | Example 1 (w/w %) |
|---|---|---|---|
| Sodium isotridecyl Sulfate [1] | 16.56 | — | — |
| C13 Alkyl sulfate from Alcohol 1 | — | 16.56 | 16.56 |
| Sodium Lauroamphoacetate [2] | 4.94 | 4.94 | — |
| Cocamidopropyl betaine [3] | — | — | 4.94 |
| Trideceth-3 (HLB = 8) [4] | 2.0 | 2.0 | 2.0 |
| Sodium Chloride | 4.75 | 4.75 | 4.75 |
| Methylchloroisothiazolinone and methylisothiazolinone [5] | 0.033 | 0.033 | 0.033 |
| EDTA [6] | 0.15 | 0.15 | 0.15 |
| Sodium Benzoate | 0.2 | 0.2 | 0.2 |
| Citric Acid, titrate (pH = ±0.2) | 5.7 | 5.7 | 5.7 |
| Water | Q.S. | Q.S. | Q.S. |
| Total Lathering Surfactant in Cleansing Phase (%) | 21.5% | 21.5% | 21.5% |
| Lamellar Phase Volume (%) | 0% | 0% | 100% |
| Young's Modulus (Pa) | 0.26 | 13 | 57 |
| Zero Shear Viscosity (Pa · s) | 10.7 | 286.9 | 1545 |

[1] prepared by sulfation of Exxal ™ 13 available from ExxonMobil.
[2] available from Cognis Chemical Corp.
[3] available from BASF Corp.
[4] Iconal TDA-3 available from BASF Corp.
[5] Kathon CG, available from Rohm & Haas Company, Philadephia, PA.
[6] Dissolvine NA 2x.

The surfactant compositions of Table II (below) were prepared by adding water in a mixing vessel. Then add the following ingredients with continuously mixing: cocamidopropyl betaine, the respective anionic surfactant sodium trideceth-2 sulfate or sodium C13 alkyl sulfate anionic surfactant, sodium lauryl sulfate, trideceth-3, sodium benzoate, and sodium chloride. Adjust pH by adding citric acid solution (50% active) to pH=5.7±0.2. Then, add Methylchloroisothiazolinone and methyl isothiazolinone. Keep mixing until homogeneous.

TABLE II

| Surfactant Phase Composition | Comparative Example 3 (w/w %) | Example 2 (w/w %) | Example 3 (w/w %) |
|---|---|---|---|
| Sodium Trideceth-2 Sulfate [1] | 6.66 | — | — |
| C13 Alkyl sulfate from Alcohol 1 | — | 13.86 | 6.66 |
| Sodium Lauryl Sulfate [2] | 6.66 | — | 6.66 |
| Cocamidopropyl betaine [3] | 6.67 | 4.14 | 6.67 |
| Trideceth-3 (HLB = 8) [4] | 1.64 | 1.64 | 1.64 |
| Sodium Chloride | 4.75 | 4.75 | 4.75 |
| Methyl chloro isothiazolinone and methyl isothiazolinone [5] | 0.05 | 0.05 | 0.05 |
| Citric Acid, titrate (pH = ±0.2) | 5.7 | 5.7 | 5.7 |
| Water | Q.S. | Q.S. | Q.S. |
| Total Lathering Surfactant in Cleansing Phase (%) | 20% | 18% | 20% |
| Lamellar Phase Volume (%) | 100% | 100% | 100% |
| Young's Modulus (Pa) | 58 | 26 | 71 |
| Zero Shear Viscosity (Pa · s) | 1767 | 713 | 1982 |

[1] available from Stepan Corporation;
[2] available from Procter & Gamble Co.;
[3] available from BASF Corp.;
[4] Iconal TDA-3 available from BASF Corp.;
[5] Kathon CG, available from Rohm & Haas Company, Philadephia, PA;

The surfactant compositions forming a cleansing phase comprise a rheology modifier to build the cleansing phase structure. The surfactant compositions can be combined with a benefit phase to form a personal care composition. The cleansing and benefit phases were combined through SpeedMixer™ (Model DAC, 400FV available from Fleck-Teck, Inc USA) at 2 000 rpm for 60 seconds.

The compositions of Table III (below) were prepared by first adding water in a mixing vessel. Then add the following ingredients with continuously mixing: sodium chloride, guar hydroxypropyltrimonium chloride, rheology modifier powers (Aqupec or Structure XL), trideceth-3, xanthan gum, cocamidopropyl betaine, sodium C13 alkyl sulfate anionic surfactant with an adequate agitation. Then add EDTA and sodium benzoate. Adjust pH by adding citric acid solution (50% active) to pH=5.7±0.2. Then, add methylchloroisothiazolinone and methyl isothiazolinone. Keep mixing until homogeneous.

The personal care compositions are prepared by adding petrolatum, glyceryl monooleate and other ingredients such as fragrance and dye into the cleansing phase composition through a SpeedMixer™ at a speed of 2,000 rpm for 60 seconds.

Figure 2:
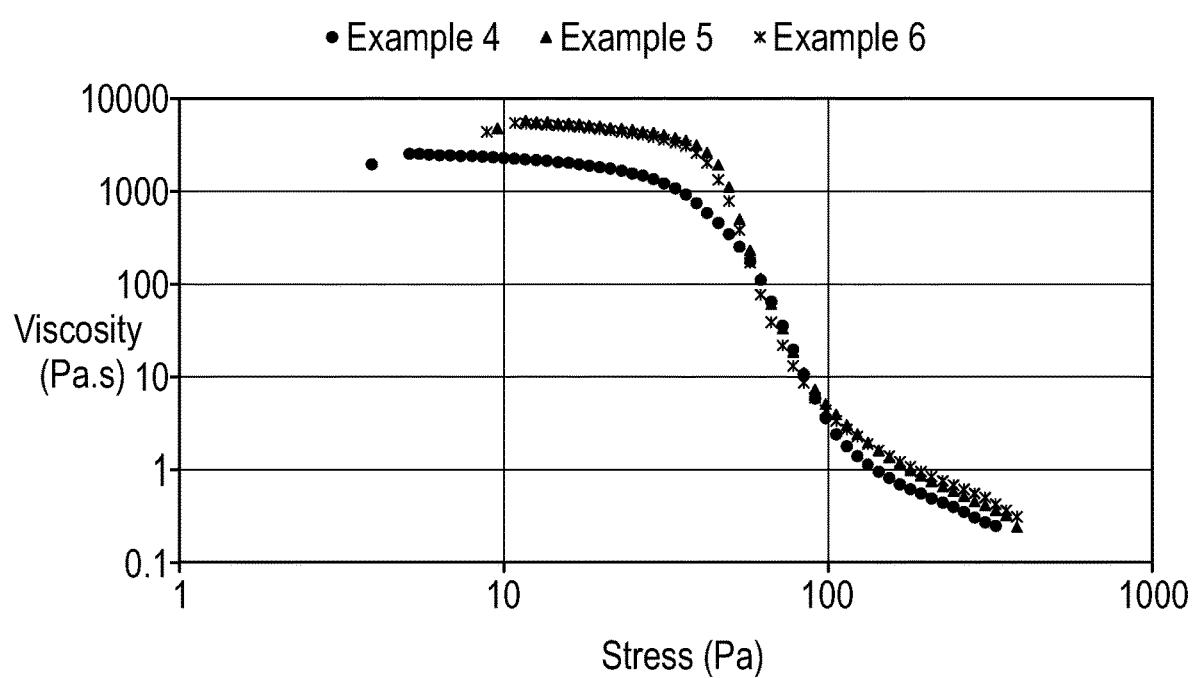
FIG. 2 is a graph of the rheology profile of the C13 alkyl sulfate anionic surfactant compositions with different rheology modifiers.

After forming the personal care compositions, their Lamellar Phase Volume, Young's Modulus, and Zero Shear Viscosity were determined utilizing the methods disclosed. The results are captured below in Table III, as well as graphically in FIG. 2. FIG. 2 displays the rheology profile as a function of shear stress of inventive examples.

Stability was assessed by measuring through Ultracentrifugation Method after aging the products at 50° C. for 10 days.

Human Use Testing

Human use testing (blinded) was performed to evaluate the performances of the compositions in terms of fragrance perception.

Two compositions were tested: Example 6 and Comparative Example 4 wherein 5.60 wt. % of C13 Alkyl sulfate from Alcohol 1 in Example 6 has been replaced with sodium isotridecyl sulfate prepared by sulfation of Exxal™ 13 available from ExxonMobil.

Subjects were non-P&G employees (n=~130/product) who use bodywash products. Products were used over a 1 week period and product performance feedback was provided by completing a questionnaire. All attributes were rated on 5-point scale (Excellent=100; Very good=75, Good=50, Fair=25, Poor=0). Data for each product was averaged and Pearson's Chi-squared test was used to compare mean ratings.

TABLE III

| Composition | Example 4 (w/w %) | Example 5 (w/w %) | Example 6 (w/w %) | Example 7 (w/w %) |
|---|---|---|---|---|
| C13 Alkyl sulfate from Alcohol 1 | 5.60 | 5.60 | 5.60 | 5.60 |
| Sodium Lauryl Sulfate [2] | 5.58 | 5.58 | 5.58 | 5.58 |
| Cocamidopropyl betaine [3] | 5.58 | 5.58 | 5.58 | — |
| Coco Betaine [3'] | | | | 5.58 |
| Trideceth-3 (HLB = 8) [4] | 1.38 | 1.38 | 1.38 | 1.38 |
| Sodium chloride | 4.22 | 4.22 | 4.22 | 4.22 |
| Acrylates/C10-C30 alkyl acrylates crosspolymer (Aqupec SER-300) | 0.06 | | | |
| Hydroxylpropyl starch phosphate (Structure XL) | — | 0.84 | — | 0.84 |
| Hydroxylpropyl starch phosphate (C*HiForm ™ A12747) | — | — | 0.84 | — |
| Guar Hydroxypropyltrimonium Chloride | 0.36 | 0.36 | 0.36 | 0.36 |
| Xanthan gum | 0.28 | 0.28 | 0.28 | 0.28 |
| Methylchloroisothiazolinone and methyl isothiazolinone [5] | 0.04 | 0.04 | 0.04 | 0.04 |
| EDTA [6] | 0.14 | 0.14 | 0.14 | 0.14 |
| Sodium Benzoate | 0.29 | 0.29 | 0.29 | 0.29 |
| Citric Acid, titrate (pH = ±0.4) | 5.8 | 5.8 | 5.8 | 5.8 |
| Petrolatum | 9.80 | 9.80 | 9.80 | 9.80 |
| Glyceryl Monooleate | 0.2 | 0.2 | 0.2 | 0.2 |
| Fragrance | 1.15 | 1.15 | 1.15 | 1.15 |
| Dye | 0.0002 | 0.0002 | 0.0002 | 0.0002 |
| Water | Q.S. | Q.S. | Q.S. | Q.S. |
| Total Lathering Surfactant Component in Composition | 16.76% | 16.76% | 16.76% | 16.76% |
| Viscosity (T(d) bar; 5 rpm, cP (mPa · s)) | 35,500 cP 35.5 Pa · s | 34,000 cP 34.0 Pa · s | 45,000 cP 45.0 Pa · s | |
| Lamellar Phase Volume (%) | 73% | 66% | 68% | 45% |
| Young's Modulus (Pa) | 98 | 197 | 217 | 70 |
| Zero Shear Viscosity (Pa · s) | 2268 | 5487 | 5745 | 1943 |

Examples 4, 5 and 6 illustrate the effectiveness of an hydrophobically modified polyacrylate like Acrylates/C10-C30 alkyl acrylates crosspolymer or an hydrophobically modified polysaccharide, particularly a modified starch for providing the higher structure and higher stability to the overall personal care composition. Another noticeable advantage of using an hydrophobically modified polysaccharide, particularly a modified starch is that the modified starch is a naturally-derived and biodegradable rheology modifier which can form sustainable personal care compositions.

Examples 6 and 7 illustrate the effectiveness of an hydrophobically modified polysaccharide such as a modified starch even when using coco betaine instead of cocamidopropyl betaine.

TABLE IV

| | | Example 5 A | Comp. Ex. 4 B |
|---|---|---|---|
| Total Responses | | 135 | 130 |
| Overall scent | Mean | 78 B | 59 |
| Pleasant scent | Mean | 80 B | 74 |
| Leaving a long-lasting scent onto skin | Mean | 60 | 55 |

* Pearson's Chi-squared test was used to compare mean ratings.
Uppercase letter indicates statistically significant difference at $\alpha = 0.05$ The data in Table IV showed that the fragrance experience was enhanced when using in the personal care composition the specific C13 alkyl sulfate anionic surfactant as recited herein over sodium isotridecyl sulfate prepared by sulfation of Exxal™ 13 available from ExxonMobil. Sodium isotridecyl sulfate comprises a mixture of branched chain 13 carbon aliphatic alkyl sulfates.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising at least a cleansing phase and a benefit phase, wherein the cleansing phase comprises an aqueous structured surfactant phase;
   wherein the cleansing phase comprises:
   (i) about 1% to about 20% by weight of the personal care composition, of a C13 alkyl sulfate anionic surfactant, wherein the C13 alkyl sulfate anionic surfactant consists of:
   (a) a linear C13 alkyl sulfate;
   (b) more than about 60% by weight of the C13 alkyl sulfate anionic surfactant of a 2-branched C13 alkyl sulfate anionic surfactant comprising:
      (i) a 2-pentyl octyl sulfate anionic surfactant, and
      (ii) more than about 25% by weight the 2-branched C13 alkyl sulfate anionic surfactant of a 2-methyl dodecyl sulfate anionic surfactant; and
   (c) at least one other branched C13 alkyl sulfate anionic surfactant;
   wherein a, b and c add up to about 100% by weight of the C13 alkyl sulfate anionic surfactant;
   (ii) about 0.1% to about 20% by weight of the personal care composition, of a zwitterionic surfactant, wherein the zwitterionic surfactant comprises a betaine; and
   (iii) a structuring system comprising:
      (iiia) optionally, a non-ionic emulsifier;
      (iiib) optionally, from about 0.01% to about 5% by weight of the personal care composition, of a rheology modifier; and
      (iiic) an electrolyte;
   wherein the benefit phase comprises: from about 0.1% to about 50%, by weight of said personal care composition, of a benefit agent.

2. The personal care composition of claim 1, wherein the C13 alkyl sulfate anionic surfactant consists of:
   (i) less than about 30% by weight of the C13 alkyl sulfate anionic surfactant of the linear C13 alkyl sulfate, and
   (ii) more than about 70% by weight of the C13 alkyl sulfate anionic surfactant of the 2-branched C13 alkyl sulfate anionic surfactant, and
   (iii) less than about 3.0% by weight of the C13 alkyl sulfate anionic surfactant of other branched C13 alkyl sulfate anionic surfactant.

3. The personal care composition of claim 1, wherein the 2-branched C13 alkyl sulfate anionic surfactant comprises:
   (i) less than about 20% by weight of the 2-branched C13 alkyl sulfate anionic surfactant of 2-pentyl octyl sulfate anionic surfactant; and
   (ii) more than about 30% by weight of the 2-branched C13 alkyl sulfate anionic surfactant of 2-methyl dodecyl sulfate anionic surfactant.

4. The personal care composition of claim 1, wherein the personal care composition is free of alkoxylated anionic sulfate surfactant.

5. The personal care composition of claim 1, wherein the zwitterionic surfactant is selected from the group consisting of cocamidopropyl betaine, coco betaine, and mixtures thereof.

6. The personal care composition of claim 1, wherein the rheology modifier is selected from the group consisting of a polyacrylate, a polysaccharide, a modified polyol, an hydrophobically modified polyacrylate, an hydrophobically modified polysaccharide, and mixtures thereof.

7. The personal care composition of claim 1, wherein the rheology modifier is selected from the group consisting of sodium polyacrylate, acrylates copolymer, acrylates/vinyl isodecanoate crosspolymer, acrylates/C10-30 alkyl acrylate crosspolymer, acrylates/C10-30 alkyl acrylate crosspolymer and comprises stearyl side chains with less than about 1% hydrophobic modification, acrylates/C10-30 alkyl acrylate crosspolymer including octyl side chains with less than about 5% hydrophobic modification, ammonium acryloyldimethyltaurate/beheneth-25 methacrylate crosspolymer, acrylates/beheneth-25 methacrylate copolymer, acrylates/steareth-20 methacrylate copolymer, and acrylates/steareth-20 methacrylate crosspolymer, PEG-150/decyl alcohol/SMDI copolymer, PEG-150/stearyl alcohol/SMDI copolymer, hydroxypropyl starch phosphate, distarch phosphate, sodium carboxymethyl starch, hydroxypropyl starch phosphate, starch, tapioca starch, xanthan gum, gellan gum, carboxymethyl cellulose, carboxymethyl hydroxyethyl cellulose, hydroxypropyl methyl cellulose, guar gum, hydroxypropyl guar, sodium alginate, and mixtures thereof.

8. The personal care composition of claim 1, wherein the non-ionic emulsifier is selected from the group consisting of glyceryl monohydroxystearate, isosteareth-2, trideceth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

9. The personal care composition of claim 1, wherein the electrolyte is selected from the group consisting of sodium chloride, ammonium chloride, sodium sulfate, ammonium sulfate, and mixtures thereof.

10. The personal care composition of claim 1, wherein the personal care composition comprises about 0.5% to about 5%, by weight of said personal care composition, of the electrolyte.

11. The personal care composition of claim 1, wherein the benefit agent is selected from the group consisting of petrolatum; lanolin; natural waxes; synthetic waxes; volatile organosiloxanes; derivatives of volatile organosiloxanes; non-volatile organosiloxanes; derivatives of non-volatile organosiloxanes; lanolin oil; lanolin esters; natural triglycerides; synthetic triglycerides; and mixtures thereof.

12. The personal care composition of claim 1, wherein the personal care composition comprises at least about 50% lamellar structure.

13. The personal care composition of claim 1, wherein the personal care composition comprises a cationic deposition polymer, wherein the cationic deposition polymer is selected from the group consisting of a cationic cellulose polymer, a cationic guar gum polymer, and mixtures thereof.

14. The personal care composition of claim 1, wherein the personal care composition comprises about 0.01% to about 5% by weight of the personal care composition, of a cationic deposition polymer.

15. The personal care composition of claim 1, wherein the C13 alkyl sulfate anionic surfactant comprises less than about 40% by weight of linear C13 alkyl sulfate.

16. The personal care composition of claim 15, wherein the 2-branched C13 alkyl sulfate anionic comprises about 25% or less by weight of the 2-branched C13 alkyl sulfate anionic surfactant of the 2-pentyl octyl sulfate anionic surfactant.

17. The personal care composition of claim 16, wherein the 2-branched C13 alkyl sulfate anionic comprises about 25% or less by weight of the 2-branched C13 alkyl sulfate anionic surfactant of the 2-pentyl octyl sulfate anionic surfactant.

* * * * *